US008372889B2

(12) United States Patent
Chan et al.

(10) Patent No.: US 8,372,889 B2
(45) Date of Patent: *Feb. 12, 2013

(54) METHODS FOR MODULATING METABOLISM

(75) Inventors: Bill Piu Chan, Beijing (CN); Gary Kwan Po Wong, Kowloon (HK); Jinxian Xu, Shanghai (CN); Francis Chi, Kowloon (HK)

(73) Assignee: Omega Biopharma (I.P.3) Limited, Kowloon (HK)

( * ) Notice: Subject to any disclaimer, the term of this patent is extended or adjusted under 35 U.S.C. 154(b) by 92 days.

This patent is subject to a terminal disclaimer.

(21) Appl. No.: 12/956,576

(22) Filed: Nov. 30, 2010

(65) Prior Publication Data
US 2011/0070272 A1 Mar. 24, 2011

Related U.S. Application Data

(63) Continuation of application No. 12/265,447, filed on Nov. 5, 2008, now Pat. No. 7,893,113, which is a continuation of application No. 11/118,737, filed on Apr. 29, 2005, now Pat. No. 7,759,398.

(60) Provisional application No. 60/567,899, filed on May 3, 2004, provisional application No. 60/637,618, filed on Dec. 20, 2004.

(51) Int. Cl.
A61K 31/13 (2006.01)
A61K 31/44 (2006.01)
A61K 31/40 (2006.01)
A61K 31/35 (2006.01)

(52) U.S. Cl. ......... 514/665; 514/355; 514/422; 514/460

(58) Field of Classification Search .................. 514/665, 514/355, 422, 460
See application file for complete search history.

(56) References Cited

U.S. PATENT DOCUMENTS

| 5,273,995 | A | 12/1993 | Roth |
| 5,401,880 | A | 3/1995 | Clark et al. |
| 5,668,117 | A | 9/1997 | Shapiro |
| 5,714,519 | A | 2/1998 | Cincotta et al. |
| 6,521,266 | B1 | 2/2003 | Mann |
| 6,630,176 | B2 | 10/2003 | Li et al. |
| 6,746,678 | B1 | 6/2004 | Shapiro |
| 7,442,720 | B2 | 10/2008 | Chan et al. |
| 2004/0033985 | A1 | 2/2004 | Chi et al. |
| 2004/0106591 | A1 | 6/2004 | Pacioretty et al. |
| 2005/0137125 | A1 | 6/2005 | Chan et al. |
| 2005/0143473 | A1 | 6/2005 | Wong et al. |
| 2005/0148674 | A1 | 7/2005 | Tang et al. |

FOREIGN PATENT DOCUMENTS

| BE | 653 101 | 12/1964 |
| FR | 2 716 625 | 2/1994 |
| FR | 2 852 959 | 3/2003 |
| GB | 2 245 491 | 8/1992 |
| JP | 05-086108 | 4/1993 |
| JP | 2002 187839 | 7/2002 |
| UA | 76438 | 10/2008 |
| WO | WO 85/02340 | 6/1985 |
| WO | WO 95/01096 | 1/1995 |
| WO | WO 96/40099 | 12/1996 |
| WO | WO 00/73266 | 12/2000 |
| WO | WO 01/95944 | 12/2001 |
| WO | WO 02/48110 | 6/2002 |
| WO | WO 2004/073700 | 9/2004 |
| WO | WO 2005/049002 | 6/2005 |
| WO | WO 2005/063226 | 7/2005 |

OTHER PUBLICATIONS

Al et al., "Effects of cysteamine on the metabolism of sugar and protein in adult geese," *Dongwuxue Yanjiu*, 2003, vol. 24, No. 4, pp. 302-304, Abstract only.
Beers et al., "Crystal-Induced Conditions," *Merck Manual*, Merck Research Laboratories, Whitehouse Station, N.J., p. 460, (2003).
Beers et al., "Diabetes Mellitus," *The Merck Manual of Medical Information*, 2003, Chapter 165, pp. 962-969.
Fisher, E A et al., "Cysteamine in Treatment of Type III Hyperlipidaemia?", *The Lancet*, Nov. 20, 1982, p. 1131-1132, National Institute of Child Health and Human Development, National Institutes of Health, Bethesda, Maryland, U.S.A.
Flechner et al., "Effects of radical scavengers on the developement of experimental diabetes," *Diabetes Research* (Edinburgh, Lothian), vol. 13, No. 2, pp. 67-73, Feb. 1990.
Gennes, J.L. et al., "Effets De Cystamine Dans Differentes Affections Allergiques," *Semaine Des Hopitaux De Paris, Expansion Scientifique Francaise* (1956), 32(56): 2850-2853.
Gyenes, L. et al., "The Properties of Fragments of Skin-Sensitizing and Blocking Antibodies as Revealed by the Prausnitz-Kuestner, Passive Cutaneous Anaphylaxis and Hemagglutination Reactions," *International Archives of Allergy and Applied Immunology* (1964), 24: 106-118.
Hansson, H.A. et al., "Insulin-like growth factor I in the pancreas of normal and diabetic adult rats," *Acta Physiologica Scandinavica.*, Apr. 1988, vol. 132, No. 4, pp. 569-576, abstract.
Kano, M. et al., "Soymilk Products Affect Ethanol Absorption and Metabolism in Rats During Acute and Chronic Ethanol Intake," *American Society for Nutritional Sciences*, 2002, pp. 238-244.
Landers, M. C. et al., "Permanent-Wave Dermatitis: Contact Allergy to Cysteamine Hydrochloride," *American Journal of Contact Dermatitis* (2003), 14(3): 157-160.
McCarty, "Inhibition of acetyl-CoA carboxylase by cystamine may mediate the hypotriglyceridemic activity of pantethine," *Med. Hypotheses*, Mar. 2001, vol. 56, No. 3, pp. 314-317.
Medline Plus, "Metaformin," www.nlm.nih.gov/medlineplus/druginfo/meds/a696005.html, 2007.
Mutschler et al., "Arzneimittelwirkungen," XP002360985, 2001, p. 414.

(Continued)

Primary Examiner — Kevin E Weddington
(74) Attorney, Agent, or Firm — Saliwanchik, Lloyd & Eisenschenk

(57) ABSTRACT

The subject invention provides materials and methods for modulating a variety of biological factors to treat biological conditions associated with the factors. In one embodiment of the invention, a cysteamine compound is administered to a patient to treat hypercholesterolemia and/or complications associated with hypercholesterolemia. In another embodiment, a cysteamine compound is administered to a patient to prevent the onset of diabetes in an at-risk patient and/or treat or prevent the onset of diabetes-associated complications.

9 Claims, 5 Drawing Sheets

OTHER PUBLICATIONS

Mutschler et al., "Arzneimittelwirkungen," XP002360985, 2001, p. 520-523.

Tennezé, L. et al., "A study of the relative bioavailability of cysteamine hydrochloride, cysteamine bitartrate and phosphocysteamine in healthy adult male volunteers," *Br. J. Clin. Pharmacol.*, Jan. 1999, vol. 47, No. 1, pp. 49-52.

Vescei et al., "Preclinical and Clinical Studies With Cysteamine and Pantethine Related to the Central Nervous System," *Prg. Neuropsychopharmacol.*, 1990, 14:835-862.

Vrba, J. et al., "Effects of cysteamine on blood pressure: possible mediation through vasopressin release," *Proc Soc. Exp. Biol. Med.*, Sep. 1988, vol. 188, No. 4, pp. 485-488, abstract.

Wall, T. L. et al., "Alcohol Metabolism in Asian American Men With Genetic Polymorphisms of Aldehyde Dehydrogenase," *Annals of Int. Med.*, 1997, 127(5):376-379.

Windholz et al., *The Merck Index*, Tenth Edition, 1983, pp. 849-850, abstract No. 5792.

Wittwer, C T et al., "Pantethine Lipomodulation: Evidence for Cysteamine Mediation in Vitro and in Vivo," *Atherosclerosis*, 1987, p. 41-47, Elsevier Scientific Publishers Ireland, Ltd.

METHODS FOR MODULATING METABOLISM

CROSS-REFERENCE TO A RELATED APPLICATION

This application is a continuation application of application Ser. No. 12/265,447, filed Nov. 5, 2008 now U.S. Pat. No. 7,893,113; which is a continuation of application Ser. No. 11/118,737, filed Apr. 29, 2005, now U.S. Pat. No. 7,759,398, which claims the benefit of U.S. Provisional Application Ser. Nos. 60/567,899 and 60/637,618, filed May 3, 2004 and Dec. 20, 2004, which are hereby incorporated by reference in their entireties, including any figures, tables, or drawings.

BACKGROUND OF THE INVENTION

Cholesterol is a naturally occurring substance in the body that is required for normal biological functions. For example, it is used for the synthesis of bile acids in the liver, the manufacture and repair of cell membranes, the production of vitamin D, and the synthesis of steroid hormones. There are both exogenous and endogenous sources of cholesterol. For example, the average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation).

Cholesterol circulates in the bloodstream via plasma lipoproteins, which are particles of complex lipid and protein composition that transport lipids in the blood. There are specific kinds of lipoproteins that contain cholesterol, namely low density lipoproteins (LDL), high density lipoproteins (HDL), and triglycerides.

LDL normally carries about 75 percent of the circulating cholesterol. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated.

As free cholesterol liberated from LDL accumulates within cells, there are three important metabolic consequences. First, there is a decrease in the synthesis of HMG-CoA reductase, the enzyme that controls the rate of de novo cholesterol synthesis by the cell. Second, there is activation of the enzyme acyl cholesterol acyltransferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from circulation.

In contrast, plasma HDL particles appear to play a major role in the reverse transport process by acting as scavengers of tissue cholesterol. HDL is also responsible for the removal of non-cholesterol lipid, oxidized cholesterol, and other oxidized products from the bloodstream. It is hypothesized that high levels of plasma HDL are not only protective against coronary artery disease, but may actually induce regression of atherosclerotic plaque (i.e., see Badimon et al., *Circulation* 86:(Suppl. III)86-94 (1992); Dansky and Fisher, *Circulation* 100:1762-3 (1999)).

Currently, an estimated 105 million American adults have undesirable (high) cholesterol levels—namely total blood cholesterol levels of 200 milligrams per deciliter (mg/dL) and higher. Of these, 42 million have cholesterol levels of 240 mg/dL or higher, and are considered a high health risk population. (Centers for Disease Control: National Center for Health Statistics as published by the American Heart Association, Heart and Stroke Statistics—2003 Update. Dallas, Tex.: AHA, 2002).

The very property that makes cholesterol useful in the cell membranes, namely its insolubility in water, also makes it potentially lethal when large amounts of cholesterol are circulating in blood. For example, high cholesterol is commonly associated with an increased risk of heart attack, atherosclerosis and circulatory disorders. In addition, a variety of diseases are caused by disorders of cholesterol catabolism, such as gallstone disease, atherosclerosis, hyperlipidemia and some lipid storage diseases.

Atherosclerosis, for example, is a slowly progressive disease characterized by the accumulation of cholesterol within the arterial wall. Compelling evidence has been submitted regarding the role of oxidized LDL in the formation of atherosclerotic lesions. (Chisolm. *Clin. Cardiol.*, 14:I-25-I-30 (1991)). As LDL becomes oxidized, its properties and mechanisms of interaction with cells are altered extensively. These changes cause the oxidized LDL to act deleteriously at various levels of artherosclerotic lesion development.

Abundant evidence indicates that lowering undesirable cholesterol levels will diminish or prevent atherosclerotic complications. In addition to a diet that maintains a normal body weight and minimizes concentrations of lipids in plasma, therapeutic strategies for lowering cholesterol levels include elimination of factors that exacerbate high cholesterol and the administration of therapeutic agents that lower plasma concentrations of lipoproteins, either by diminishing the production of lipoproteins or by enhancing the efficiency of their removal from plasma. For example, recent studies have shown that taking antioxidants such as vitamin E or beta carotene, reduces an individual's risk of heart attack presumably by preventing the oxidation of LDL (See *NY Times*, p. A9, cols. 1-6, Nov. 19, 1992).

Additional methods for maintaining a desirable/healthy serum cholesterol levels include the use of cholesterol-lowering agents (i.e., lavostatin, pravastatin, simvastatin, fluvastatin, and atorvastatin). Several trials of the long-term effects of cholesterol-lowering drugs on patients have shown reduced death from and incidence of heart disease. (See Lipid Research Clinics Investigators, *Arch Intern Med.* 152:1399-1410 (1992)). Although these drugs can produce significant reductions in serum cholesterol, most if not all have undesirable side effects.

Although it has been demonstrated that estrogens have beneficial effects on serum LDL, long-term estrogen therapy has been implicated in a variety of disorders, including an increase in the risk of uterine cancer and possibly breast cancer. Recently suggested therapeutic regimens, which seek to lessen the cancer risk, such as administering combinations of progestogen and estrogen, cause the patient to experience regular bleeding, which is unacceptable to most older women. Furthermore, combining progesterone with estrogen seems to blunt the serum cholesterol lowering effects of estrogen. Concerns over the significant undesirable effects associated with estrogen therapy, support the need to develop alternative therapies for lowering undesirable cholesterol levels, which generate desirable effects on serum LDL but do not cause undesirable effects.

Diabetes, which is often linked with high cholesterol, is a chronic disease that has no cure. Currently, about 18.2 million people or 6.3% of the population in the United States have diabetes. While roughly 13 million have been diagnosed, it is estimated that 5.2 million people are not aware that they have the disease. As the 6th leading cause of death by disease in 2000, diabetes is costing the US health care system an estimated $132 billion annually. National Diabetes Information Clearinghouse, NIH Publication No. 04-3892, November 2003. More serious than the economic costs associated with diabetes are the decrease in quality of life, serious health complications/consequences, and deaths associated with diabetes.

With about 12,000 to 24,000 new cases each year, diabetes is the leading cause of new cases of blindness in adults ages 20-74. Diabetes is also the leading cause of end-stage renal disease, accounting for about 44% of new cases annually. In 2001 alone, approximately 42,800 people initiated treatment for end stage renal disease (kidney failure) because of diabetes. About 60-70 percent of people with diabetes have mild to severe forms of diabetic nerve damage, which, in severe forms, can lead to lower limb amputations. In fact, more than 60% of non-traumatic, lower limb amputations are performed on persons with diabetes. In 2002-2003, about 82,000 non-traumatic, lower limb amputations were performed on persons with diabetes. People with diabetes are 2 to 4 times more likely to suffer a stroke. Moreover, adults with diabetes have heart disease death rates about 2 to 4 times higher than those without diabetes.

Diabetes is a group of diseases characterized by high blood glucose levels, which result from defects in insulin production, insulin action, or both. Because diabetes can remain undiagnosed for years, many people become aware that they have diabetes only after the development of one of its life-threatening complications. Although the cause of diabetes is still unknown, it is well-accepted that both genetics and environmental factors, such as obesity and lack of exercise, are important factors.

One group of diabetes, Type 1 diabetes (or insulin-dependent diabetes mellitus or juvenile-onset diabetes), develops when the body's immune system destroys pancreatic cells that make the hormone insulin, which regulates blood glucose levels. Type 1 diabetes usually occurs in children and young adults; although disease onset can occur at any age. Type 1 diabetes accounts for about 5 to 10 percent of all diagnosed cases of diabetes. Risk factors for Type 1 diabetes include autoimmune, genetic, and environmental factors. Individuals diagnosed with Type 1 diabetes require daily delivery of insulin via injections or pumps.

Another group of diabetes, Type 2 diabetes (or non-insulin-dependent diabetes mellitus or adult-onset diabetes), is a metabolic disorder resulting from the body's inability to make enough, or properly use, insulin. This disease usually begins as insulin resistance, a disorder in which the cells do not use insulin properly, and as the need for insulin rises, the pancreas gradually loses its ability to produce insulin. Type 2 diabetes is the most common form of the disease accounting for 90-95 percent of diabetes. Type 2 diabetes is nearing epidemic proportions, due to an increased number of older Americans, and a greater prevalence of obesity and a sedentary lifestyle.

Gestational diabetes refers to a form of glucose intolerance that is diagnosed in pregnant women. During pregnancy, gestational diabetes requires treatment to normalize maternal blood glucose levels to avoid complications in the infant. A percentage (5-10 percent) of women with gestational diabetes have Type 2 diabetes after pregnancy. Women who have had gestational diabetes also have a 20-50 percent chance of developing diabetes in the next 5-10 years.

Hyperinsulinemia refers to the overproduction of insulin by pancreatic cells. Often, hyperinsulinemia occurs as a result of insulin resistance, which is a condition defined by cellular resistance to the action of insulin. Insulin resistance, as defined above, is a state/disorder in which a normal amount of insulin produces a subnormal biologic (metabolic) response. For example, in insulin-treated patients with diabetes, insulin resistance is considered to be present whenever the therapeutic dose of insulin exceeds the secretory rate of insulin in normal person.

Hypertension has been associated with hyperinsulinemia. Insulin acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Impaired glucose homeostasis (or metabolism) refers to a condition in which blood sugar levels are higher than normal but not high enough to be classified as diabetes. There are two categories that are considered risk factors for future diabetes and cardiovascular disease. Impaired glucose tolerance (IGT) occurs when the glucose levels following a 2-hour oral glucose tolerance test are between 140 to 199 mg/dl. IGT is a major risk factor for Type 2 diabetes and is present in about 11 percent of adults, or approximately 20 million Americans. About 40-45 percent of persons age 65 years or older have either Type 2 diabetes or IGT. Impaired fasting glucose (IFG) occurs when the glucose levels following an 8-hour fasting plasma glucose test are greater than 110 but less than 126 mg/dl.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson. J. et al., (ed.), *Disorders of Lipid Metabolism*, Chapter 23, Textbook of Endocrinology, 9th Edition, (W. B. Sanders Company, Philadelphia, Pa. U.S.A. 1998).

Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with nondiabetic subjects (see, e.g., Garcia, M. J. et al., "Morbidity and mortality in diabetics in the Framingham population. Sixteen year follow-up study," *Diabetes*, 23:105-11 (1974); and Laakso, M. and Lehto, S., "Epidemiology of risk factors for cardiovascular disease in diabetes and impaired glucose tolerance," *Atherosclerosis*, 137 Suppl: S65-73 (1998)). Several lipoprotein abnormalities have been described among diabetic subjects (Howard B., et al., "Lipoprotein composition in diabetes mellitus," *Artherosclerosis*, 30:153-162 (1978)).

Hyperglycemia, a common feature of diabetes, is caused by decreased glucose utilization by liver and peripheral tissues and an increased glucose production by liver. Glucokinase (GK), the major glucose phosphorylating enzyme in the liver and the pancreatic $\beta$-cells, plays an important role in regulating blood glucose homeostasis. Notably, the levels of this enzyme are lowered in patients with Type 2 diabetes (Caro, J. F. et al., *Hormone metabolic Res.*, 27; 19-22, 1995) and in some diabetic animal models (Barzilai, N. and Rossetti, L. *J. Biol. Chem.*, 268:25019-25025, 1993).

As supported above, virtually every major organ system in the body is damaged by diabetes. Complications can include blindness, kidney failure, heart disease, stroke, amputation of extremities, loss of nerve sensation, early loss of teeth, high-risk pregnancies and babies born with birth defects. Currently, insulin injection is the only treatment method available for the over 1.5 million Type 1 diabetics and becomes the eventual course of treatment for many of the more than 16 million Type 2 diabetics in the United States. Treatment of Type 2 diabetes usually consists of a combination of diet, exercise, oral hypoglycemic agents, e.g., thiazolidinediones, and in more severe cases, insulin. However, the clinically available hypoglycemic agents can have side effects that limit their use, or an agent may not be effective with a particular patient.

In the case of Type I, insulin is usually the primary course of therapy. In spite of the early discovery of insulin and its subsequent widespread use in the treatment of diabetes, and the later discovery of and use of sulfonylureas, biguanides and thiazolidinediones, such as troglitazone, rosiglitazone or pioglitazone, as oral hypoglycemic agents, the treatment of diabetes remains less than satisfactory. Nutritional therapies that positively impact glucose uptake in the face of insulin insufficiency would have a major impact on the long term treatment costs associated with diabetic care.

Adiponectin or Acrp30 (Hu, E. et al, "AdipoQ is a novel adipose-specific gene dysregulated in obesity," *J. Biol. Chem.*, 271:10697-10703 (1996)) is an adipocyte-derived hormone with multiple biological functions. It has been reported that obesity, Type 2 diabetes and coronary heart disease are associated with decreased plasma adiponectin levels, and that adiponectin may have putative anti-atherogenic properties in vitro (Ouchi, N. et al, "Adipocyte-derived plasma protein, adiponectin, suppresses lipid accumulation and class A scavenger receptor expression in human monocyte-derived macrophages," *Circulation*, 103:1057-1063 (2001); Yokota, T. et al, "Adiponectin, a new member of the family of soluble defense collagens, negatively regulates the growth of myelomonocytic progenitors and the functions of macrophages," *Blood*, 96:1723-1732 (2000)).

It has also been reported that an acute increase in circulating levels of Acrp30 lowers hepatic glucose production (Berg, A. H. et al, "The adipocyte-secreted protein Acrp30 enhances hepatic insulin action," *Nat. Med.*, 7:947-953 (2001); Combs, T. P. et al, "Endogenous glucose production is inhibited by the adipose-derived protein Acrp30," *J. Clin. Invest.* 108:1875-1881 (2001). Moreover, it has been reported that globular Acrp30 increases fatty acid oxidation in muscle, and causes weight loss in mice (Fruebis, J. et al, "Proteolytic cleavage product of 30-kDa adipocyte complement-related protein increases fatty acid oxidation in muscle and causes weight loss in mice," *Proc. Natl. Acad. Sci. USA*, 98:2005-2010 (2001)). Further, it has been reported that treatment with adiponectin consisting solely of the globular domain (globular adiponectin or gAd) increases fatty acid oxidation in muscle, thereby ameliorating insulin resistance in lipoatrophic mice and obese mice, while treatment with full-length adiponectin also ameliorates though less than with gAd (Yamauchi, T. et al, "The fat-derived hormone adiponectin reverses insulin resistance associated with both lipoatrophy and obesity," *Nat. Med.*, 7:941-946 (2001)).

Recently it has been reported that adiponectin acutely activates AMP kinase (AMPK) in skeletal muscle, thus stimulating fatty acid oxidation and glucose uptake (Yamauchi, T. et al, "Adiponectin stimulates glucose utilization and fatty-acid oxidation by activating AMP-activated protein kinase," *Nat. Med.*, 8:1288-1295 (2002)), and that adiponectin chronically activates PPAR$\alpha$, resulting in increased fatty acid oxidation but reduced tissue TG content in the muscles, with these effects being greater with gAd than with full-length adiponectin (Yamauchi, T. et al, "Globular adiponectin protected ob/ob mice from diabetes and ApoE-deficient mice from atherosclerosis," *J. Biol. Chem.*, 278:2461-2468 (2002)). Interestingly, in the liver full-length adiponectin alone acutely activates AMPK, causing a reduction in gluconeogenesis-associated molecules and stimulating fatty-acid oxidation, and moreover full-length adiponectin alone chronically activates AMPK, stimulating fatty-acid oxidation and reducing tissue TG levels in the liver. All these changes serve to enhance insulin sensitivity in vivo (Yamauchi, T. et al, *Nat. Med.*, 8:1288-1295 (2002); Yamauchi, T. et al, *J. Biol. Chem.*, 278:2461-2468 (2002)).

The findings above suggest adiponectin's potential involvement in obesity, cardiovascular disease, and diabetes. Production and circulating adiponectin concentrations are suppressed in obese mice and humans (Hu, et al., *J. Biol. Chem.*, 271:10697-107032 (1996); Arita, et al., "Paradoxical decrease of an adipose-specific protein, adiponectin, in obesity," *Biochem. Biophys. Res. Commun.*, 257:79-83 (1999)). Low plasma levels of adiponectin may be a risk factor in coronary heart disease and concentrations are also significantly reduced in Type 2 diabetes (Ouchi, et al., Circulation. 100:2473-2476 (1999); Hotta, et al., Diabetes. 50:1126-1133 (2001)). The ability of adiponectin to lower glucose and reverse insulin resistance suggests that it may 30 have application as a diabetes drug (Yamauchi, et al., Nat. Med. 7:941-946 (2001); Berg, et al. Nat. Med. 7:947-953 (2001)). Furthermore, a proteolytically cleaved fragment of adiponectin was shown to cause weight loss in obese animals (Fruebis, et al., Proc. Natl. Acad. Sci. USA. 98:20(15-2010 (2001)). This protein directly or indirectly affects at least four cell types. Adiponectin modulates NF-.kappa.B mediated signals in human aortic endothelial cells, presumably accounting for their reduced adhesiveness for monocytes (Ouchi, et al., "Adiponectin, an adipocyte-derived plasma protein, inhibits endothelial NF-kappaB signaling through a cAMP-dependent pathway," *Circulation*, 102:1296-1301 (2000)). The protein suppresses differentiation of myeloid progenitor cells and has discrete effects on two monocyte cell lines (Yokota, Blood. 96:1723-1732 (2000)). Adiponectin may also induce metabolic changes in hepatocytes (Yamauchi, et al., 2001; Berg, et al. 2001).

Insofar as is known, cysteamine compounds have not been previously reported as being useful in modulating biological factors such as adiponectin levels and blood uric acid levels to treat abnormally functioning metabolism (i.e., glucose or lipid metabolism).

BRIEF SUMMARY OF THE INVENTION

The subject invention provides materials and methods for modulating at least one biological factor via the administration of a cysteamine compound to treat a biological condition, such as abnormal glucose or lipid metabolism. Contemplated biological factors modulated in accordance with the subject invention include, but are not limited to, insulin-like growth factors (such as insulin-like growth factor 1 or IGF-1), blood sugar levels, insulin levels, C peptide levels, triglyceride levels, free fatty acid levels, blood uric acid levels, microalbuminuria levels, glucose transporter expression, adiponectin levels, total serum cholesterol levels, high density lipoprotein (HDL) levels, and low density lipoprotein (LDL) levels.

Biological conditions that can be treated via the administration of a cysteamine compound as disclosed herein include, but are not limited to, hypercholesterolemia; hyperinsulinemia; dysglycemia; hyperuricemia; high triglyceride levels (including high LDL levels); obesity, cardiovascular disease; hypertension; hyperglycemia; glucose intolerance; low HDL levels; diabetes (Types 1 and 2); as well as any other symptoms, complications, conditions, or diseases associated with either high cholesterol or diabetes. In accordance with the subject invention, the administration of a cysteamine compound to a patient can delay or even prevent the development of such biological conditions (such as diabetes or high cholesterol) and any associated symptoms, complications, conditions, or diseases associated with said biological condition.

The present invention provides methods for the treatment and/or prevention of abnormal lipid metabolism, or for preventing, delaying, and/or treating the development of abnormal lipid metabolism-related complications. More specifically, the subject invention provides materials and methods for treating and/or preventing high cholesterol or hypercholesterolemia, or for preventing, delaying, and/or treating the development of hypercholesterolemia (or high cholesterol)-related complications, through the administration of a cysteamine compound to a patient. Specifically exemplified herein is the use of a cysteamine compound to lower total blood cholesterol levels, free fatty acid levels, LDL levels and/or triglyceride levels. Further, a cysteamine compound can be administered to a patient to increase HDL levels.

The subject invention further provides materials and methods for treating diabetes. In a preferred embodiment, the invention provides unique materials and methods for the treatment and/or prevention of diabetes related symptoms as well as the prevention or delay in development of diabetes-related complications, conditions, or diseases. For example, complications, conditions, or diseases such as background diabetic retinopathy, macular edema, cataracts, necrobiosis lipoidica, obesity, hyperinsulinemia, hypertension, hyperglycemia, diabetic dermopathy, fungal infections, cardiovascular disease, congestive heart failure, kidney disease, dysglycemia, hyperuricemia, high triglycerides, high HDL levels, obesity (particularly of the abdominal type), and diabetic neuropathy, all of which are commonly associated with diabetes, can be prevented or treated through the administration of a cysteamine compound, in accordance with the subject invention.

In a preferred embodiment, a cysteamine compound is administered to a patient who has no observable symptoms of a biological condition but has been determined to be susceptible to developing the biological condition (hereinafter such a patient is referred to as an "at-risk patient"). In a specific embodiment, a patient is assessed to identify the risk of developing Type 2 diabetes prior to the administration of a cysteamine compound. Various markers have recently been identified as important markers that predate the clinical onset of Type 2 diabetes. Immunological markers that can be detected using methods known to the skilled artisan to identify an at-risk patient for Type 2 diabetes include, but are not limited to, autoantibodies to insulin (IAA); glutamic acid decarboxylase (GAD); and autoantibodies to islet cells (ICA), such as an islet cell member of the receptor type of the tyrosine phosphate family termed IA-2. Methods for identifying at-risk patients for Type 2 diabetes via the detection of such markers, which can be used in accordance with the subject invention, include but are not limited to U.S. Pat. Nos. 6,391,651 and 6,316,209.

In another embodiment a patient is assessed to identify the risk of developing high cholesterol prior to the administration of a cysteamine compound. Various markers have recently been identified as important markers that predate the clinical onset of high cholesterol (or hypercholesterolemia or hyperlipidemia). Markers that can be detected using methods known to the skilled artisan to identify an at-risk patient for high cholesterol include, but are not limited to, C-reactive protein (CRP) (see Yeh, E. T., "C-reactive protein is an essential aspect of cardiovascular risk factor stratification," *Can J Cardiol.*, 20(Suppl B):93-96B (August 2004); apolipoprotein CIII; and plasma homocysteine levels (see Geisel, J et al., "The impact of hyperhomocysteinemia as a cardiovascular risk factor in the prediction of coronary heart disease," *Clin Chem Lab Med.*, 41(11):1513-7 (2003)). Methods for identifying at-risk patients for high cholesterol (or hypercholesterolemia or hyperlipidemia) via the detection of such markers, which can be used in accordance with the subject invention, include but are not limited to U.S. Patent Application No. 2004/0198656.

Additional factors that can be used, alone or in combination, to determine whether an at-risk patient is predisposed to developing hypercholesterolemia include, without limitation, heredity (i.e., familial hypercholesterolemia), high blood pressure, smoking activity, alcoholic consumption, diabetes, obesity, physical inactivity, age and sex (i.e., post-menopausal women over the age of 50), and stress.

In a method of use, a cysteamine compound is administered to a patient prior to or after diagnosis of a biological condition (i.e., diabetes or high cholesterol) to treat, delay the onset of, or ameliorate symptoms associated with the biological condition and/or complications associated with the biological condition. According to the subject invention, the compositions of the invention can be administered at any time (such as at a non-scheduled or undetermined time) to elicit a therapeutic effect.

According to the present invention, for the first time it has been discovered that the administration of a cysteamine compound to a patient can increase glucose transporter (glut4) expression in liver, muscle, adipocytes, and other tissues. In addition, the administration of a cysteamine compound to a patient decreases insulin-like growth factor 1 (IGF-1), decreases C peptide, decrease blood uric acid levels, decrease in microalbuminuria levels, and increases adiponectin levels. Modulation of these, and other, biological factors by administering a cysteamine compound can improve patient insulin sensitivity, decrease hyperinsulinemia, decrease homeostasis model assessment (HOMA) values, decrease hyperglycemia, and decrease glucose intolerance.

Also in accordance with the subject application, the administration of a cysteamine compound to a patient has been observed to modulate biological factors that may represent or develop into diabetes-related or high cholesterol-related complications or conditions. As noted above, it has been discovered that that administration of a cysteamine compound to a patient can affect insulin levels, glucose or blood sugar levels, C-peptide levels, insulin-like growth factors, blood uric acid levels, free fatty acid levels, adiponectine levels, glut4 expression, triglyceride levels, high density lipoprotein (HDL) levels, low density lipoprotein (LDL) levels, and microalbuminuria levels in a patient. In particular, administration of a cysteamine compound to a patient can: decrease hyperinsulinemia, decrease insulin-like growth factor 1 (IGF-1), decrease C-peptide levels, increase glut 4 expression in tissues, decrease free fatty acid levels, decrease blood uric acid levels, increase adiponectine levels, decrease triglyceride levels, decrease LDL levels, increase HDL levels, and decrease microalbuminuria levels.

Because all of these biological factors are relevant to the diagnosis and/or development of diabetes or high cholesterol related symptoms, complications, or conditions (see Reist, G C et al., "Changes in IGF activities in human diabetic vitreous," *Diabetes,* 53(9):2428-35 (September 2004); Janssen J A and Lamberts, S W, "The role of IGF-I in the development of cardiovascular disease in Type 2 diabetes mellitus: is prevention possible?" *Eur J Endocrinol.,* 146(4):467-77 (2002); Chakrabarti, S et al., "C-peptide and retinal microangiopathy in diabetes," *Exp Diabesity Res.,* 5(1):91-6 (January-March 2004); Gottsater, A. et al., "Plasma adiponectin and serum advanced glycated end-products increase and plasma lipid concentrations decrease with increasing duration of Type 2 diabetes," *Eur J Endocrinol.,* 151(3):361-6 (September 2004); Tseng, C H., "Independent association of uric acid levels with peripheral arterial disease in Taiwanese patients with Type 2 diabetes," *Diabet Med.,* 21(7):724-9 (July 2004); Liese, A D et al., "Microalbuminuria, central adiposity and hypertension in the non-diabetic urban population of the MONICA Augsburg survey 1994/95," *J Hum Hypertens.,* 15(11):799-804 (2001); and Wollesen, F. et al., "Peripheral atherosclerosis and serum lipoprotein(a) in diabetes," *Diabetes Care.,* 22(1):93-8 (1999)), administration of a cysteamine compound can be used as described to treat diabetes or high cholesterol related complications and conditions as well as prevent the development of such biological conditions in an at-risk patient. Contemplated complications to be treated or prevented in accordance with the present invention include, but are not limited to, hyperinsulinemia, dysglycemia, hyperuricemia, high triglycerides, increase HDL cholesterol, hypertension, obesity, atherosclerosis, cardiovascular disease, cerebrovascular thrombosis or hemorrhage, stroke, angina, coronary thrombosis, coronary heart disease (i.e., heart failure), intermittent claudication, and ischemia in the limbs.

In accordance with the subject invention, administration of a cysteamine compound to a patient prior to or at the onset of diabetes diagnosis can alter the patient's metabolism so that diabetes of high cholesterol does not develop, or develops to a lesser extent than would be observed in the absence of the cysteamine compound. By modulating the biological factors mentioned above, the materials and methods of the invention may treat and/or prevent biological conditions (such as diabetes or high cholesterol) and corresponding symptoms as well as treat and/or prevent biological condition-related complications or conditions. For example, subjects with abnormal glucose metabolism or insulin resistance, but not full-blown diabetes (e.g., obese patients), should not develop diabetes due to improved glucose utilization and insulin resistance as a result of cysteamine activity (i.e., observed cysteamine modulation of glucose transporters and adiponectin and lipid metabolism).

In accordance with the subject invention, the daily dosage amount of a cysteamine compound administered to a patient diagnosed with diabetes or suffering from complications, conditions, or diseases associated with diabetes is about 0.1 mg to about 1,000 mg/kg of patient body weight (BW) of a cysteamine compound.

In one embodiment, cysteamine is administered daily to a patient at unscheduled times to treat diabetes, wherein the therapeutically effective amount of cysteamine is about 0.1 mg to 400 mg per kilogram of patient BW or an equivalent molar quantity of a cysteamine compound. In another embodiment, cysteamine hydrochloride is administered daily to a patient at unscheduled times to treat diabetes, wherein the therapeutically effective amount of cysteamine hydrochloride is about 1.0 mg to 600 mg/kg of BW or an equivalent molar quantity of a cysteamine compound. Preferably, a daily dose of less than about 30 mg/kg of BW of cysteamine, or an equivalent molar quantity of a cysteamine compound, is administered to a patient to treat diabetes in accordance with the present invention.

In an embodiment of the subject invention, the daily dosage amount of a cysteamine compound administered to a patient to treat and/or prevent hypercholesterolemia, or delay the development of hypercholesterolemia-related complications, can be about 1 mg/kg of body weight to 300 mg/kg of body weight. Preferably, a cysteamine compound is administered at about 5 mg/kg of body weight to 150 mg/kg of body weight per day at unscheduled times. In a more preferred embodiment, about 10 mg to 100 mg of cysteamine hydrochloride per kilogram of body weight, or an equivalent molar quantity of a cysteamine compound, is administered daily to a patient.

A cysteamine compound can be administered alone or concurrently with other known cholesterol-lowering agents or therapeutic methods. Contemplated cholesterol-lowering agents or therapeutic methods include, without limitation, altering dietary intake, increasing physical activity, weight loss, hormone replacement therapy in post-menopausal women, and medicines (i.e., lovastatin, pravastatin, simvastatin, fluvastatin, atorvastatin, bile acid resins, nicotinic acid or niacin, and fibrates).

In another embodiment of the invention, a cysteamine compound is administered to a patient diagnosed with diabetes to treat diabetes as well as prevent and/or decrease the severity of diabetes-related complications. In a related embodiment, a cysteamine compound is administered in combination with other known agents that are used to treat diabetes (i.e., insulin, sulfonylureas, biguanides, α-glucosidase inhibitors, thiazolidinediones, meglitinides, D-phenylalanine) to either prevent and/or treat diabetes and diabetes-related complications.

In another embodiment, compositions of the invention comprising a cysteamine compound are provided that include "inclusion compound host materials" that fix gases, liquids, or compounds as inclusion complexes for handling in solid form and for ease of subsequent release (i.e., by exposure to an alkaline environment, by the action of a solvent, or by melting).

DETAILED DISCLOSURE OF THE INVENTION

Figure 1:
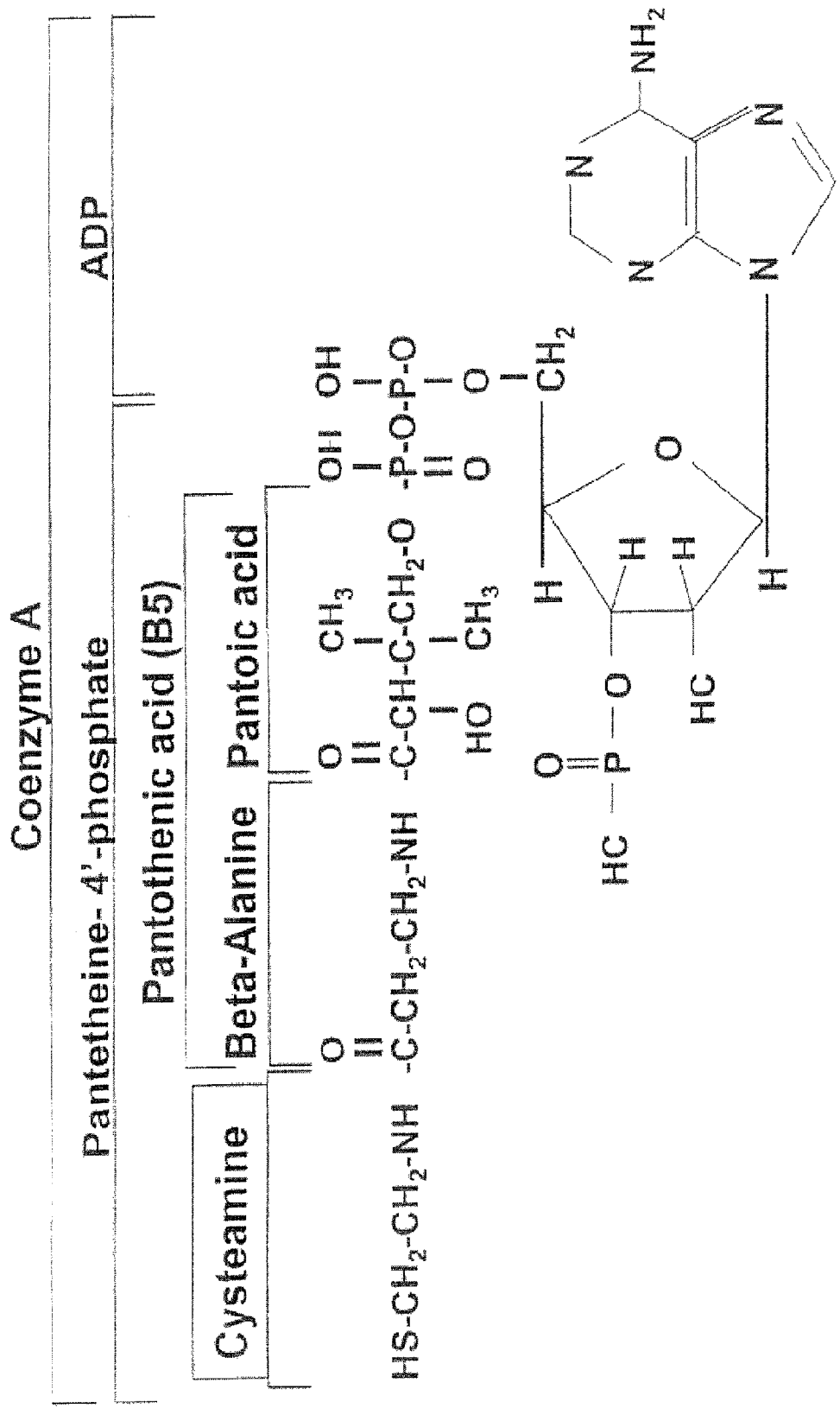
FIG. 1 shows a metabolic pathway of cysteamine.

The subject invention provides materials and methods for modulating at least one biological factor via the administration of a cysteamine compound to treat a biological condition, such as abnormal glucose or lipid metabolism. Contemplated biological factors modulated in accordance with the subject invention include, but are not limited to, insulin-like growth factors (such as insulin-like growth factor 1 or IGF-1), blood sugar levels, insulin levels, C peptide levels, triglyceride levels, free fatty acid levels, blood uric acid levels, microalbuminuria levels, glucose transporter expression, adiponectin levels, high density lipoprotein (HDL) levels, and low density lipoprotein (LDL) levels.

Preferably, the subject invention provides materials and methods for treating or preventing the onset of high cholesterol (or hypercholesterolemia or hyperlipidemia) in a patient and/or treating or delaying/preventing the onset of complications, conditions, or diseases associated with high cholesterol (or hypercholesterolemia or hyperlipidemia). The subject invention also preferably treats and/or prevents the development of diabetes and diabetes-related symptoms as well as complications, conditions, and/or diseases associated with diabetes.

The term "treatment" or any variation thereof (i.e., treat, treating, etc.), as used herein, refers to any treatment of a patient diagnosed with a biological conditions, such as hypercholesterolemia or diabetes, using the materials and/or methods of the invention. The term treatment, as used herein, includes: (i) preventing or delaying the presentation of symptoms associated with the biological condition of interest in an at-risk patient who has yet to display symptoms associated with the biological condition; (ii) ameliorating the symptoms associated with the biological condition of interest in a patient diagnosed with the biological condition; (iii) preventing, delaying, or ameliorating the presentation of symptoms associated with complications, conditions, or diseases associated with the biological condition of interest (i.e., hypercholesterolemia and/or diabetes) in either an at-risk patient or a patient diagnosed with the biological condition; and/or (iv) relieving the condition (i.e. causing regression of hypercholesterolemia and/or diabetes or associated complications, conditions or diseases).

"Hypercholesterolemia" (also known as high cholesterol, hypercholesteremia, hyperlipidemia, or hypercholesterinemia), as used herein, refers to a condition characterized by levels of total serum cholesterol, or of LDL and/or triglycerides, which are elevated as compared to levels that are considered normal by those of ordinary skill in the art. For example, the National Institutes of Health have described normal or optimal levels of total serum cholesterol to be less than 200 mg of cholesterol per dL of blood and normal or optimal levels of LDL to be less than 100 mg of LDL per dL of blood. According to certain embodiments of the present invention, hypercholesterolemia includes conditions in which total serum cholesterol levels are about 200 mg/dL or greater; and LDL levels are 100 mg/dL, or greater. As understood by the skilled artisan, characteristics used in diagnosing hypercholesterolemia are subject to change and the latest standards, such as those disclosed by the National Institutes of Health, can be used to define hypercholesterolemia as provided in the present invention.

The identification of those patients who are in need of treatment for hypercholesterolemia is well within the knowledge and ability of one skilled in the art. For example, individuals who have serum cholesterol levels or LDL cholesterol levels, as determined by clinical laboratory tests, which are elevated over that considered normal by those of ordinary skill in the art, are patients in need of treatment for hypercholesterolemia. By way of further example, a clinician skilled in the art can readily identify, by the use of clinical tests, physical examination, and medical/family history, those patients who are suffering from hypercholesterolemia as well as those who are predisposed to developing hypercholesterolemia and thus readily determine if an individual is a patient in need of treatment for hypercholesterolemia.

"Arteriosclerosis" as used herein, refers to a disease state characterized by the development and growth of atherosclerotic lesions or plaque. The identification of those patients who are in need of treatment for atherosclerosis is well within the knowledge and ability of one skilled in the art. For example, patients who are either suffering from clinically significant atherosclerosis or who are at risk of developing atherosclerosis as a result of hypercholesterolemia are considered patients in need of treatment for a complication associated with hypercholesterolemia.

As used herein, the term "diabetes" is intended to mean all diabetic conditions, including, without limitation, diabetes mellitus, genetic diabetes, Type 1 diabetes, Type 2 diabetes, and gestational diabetes. The term "diabetes" also refers to the chronic disease characterized by relative or absolute deficiency of insulin that results in glucose intolerance. Type I diabetes is also referred to as insulin dependent diabetes mellitus (IDDM) and also includes, for example, juvenile-onset diabetes mellitus. Type I is primarily due to the destruction of pancreatic β-cells. Type 2 diabetes mellitus is also known as non-insulin dependent diabetes mellitus (NIDDM) and is characterized, in part, by impaired insulin release following a meal. Insulin resistance can also be a factor leading to the occurrence of Type 2 diabetes mellitus. Genetic diabetes is due to mutations which interfere with the function and regulation of β-cells.

Diabetes, as used herein, is characterized as a fasting level of blood glucose greater than or equal to about 130 mg/dl or as a plasma glucose level greater than or equal to about 180 mg/dl as assessed at about 2 hours following the oral administration of a glucose load of about 75 g or following a meal. As understood by the skilled artisan, characteristics used in identifying diabetes are subject to change and the latest standards, such as those disclosed by the World Health Organization, can be used to define diabetes as provided in the present invention.

The term "diabetes" is also intended to include those individuals with hyperglycemia, including chronic hyperglycemia, impaired glucose homeostasis or tolerance, and insulin resistance. Plasma glucose levels in hyperglycemic individuals include, for example, glucose concentrations greater than normal as determined by reliable diagnostic indicators. Such hyperglycemic individuals are at risk or predisposed to developing overt clinical symptoms of diabetes mellitus.

As used herein, the term "hypercholesterolemia complication(s)" refers to medical/clinical problems that occur more often in patients diagnosed with hypercholesterolemia than the general population. As contemplated herein, complications associated with hypercholesterolemia include, without limitation, cardiovascular disease (i.e., arteriosclerosis, atherosclerosis, stroke, high blood pressure, angina, heart attack/failure, cardiac arrhythmia), pancreatitis, diabetes, obesity, and cerebrovascular disease (i.e., hemorrhagic stroke).

As used herein, the term "diabetic complication(s)" refers to medical/clinical problems that occur more often in patients diagnosed with diabetes. As contemplated herein, diabetic complications include medical/clinical problems that stem from changes in blood vessels and/or nerves as a result of diabetes. These include, and are not limited to, skin conditions (i.e., bacterial infections, fungal infections, diabetic dermopathy, necrobiosis lipoidica, diabeticorum (i.e., bullosis diabeticorum), eruptive xanthomatosis, allergic skin reactions, digital sclerosis, disseminated granuloma annulare, and acanthosis nigricans), gum disease, eye disorders (i.e., glaucoma, cataracts, retinopathy, kidney disease, neuropathy (i.e., systemic neuropathy, distal systemic polyneuropathy, proximal neuropathy, femoral neuropathy, neuropathic antrhropathy, cranial neuropathy, authonomic neuropathy, compression neuropathy, and diabetic amyotrophy), hyperinsulinemia, dysglycemia, hyperuricemia, obesity, hypercholesterolemia, cardiovascular diseases/disorders (i.e., hypertension, heart disease, heart attack, stroke).

The term "patient," as used herein, describes an organism, including mammals, to which treatment with the compositions according to the present invention is provided. Mammalian species that benefit from the disclosed methods of treatment include, but are not limited to, apes, chimpanzees, orangutans, humans, monkeys; and domesticated animals (i.e., pets) such as dogs, cats, mice, rats, guinea pigs, and hamsters.

"Concurrent administration" and "concurrently administering," as used herein, includes administering a compound or therapeutic method suitable for use with the methods of the invention (administration of a cysteamine compound) in the modulation of biological factors to treat a specific biological condition. In certain embodiments, a cysteamine compound is concurrently administered with an additional therapeutic agent known to be useful in treating diabetes or hypercholesterolemia. For example, according to the subject invention, a cysteamine compound can be concurrently administered with therapeutic methods or agents useful in the treatment of hypercholesterolemia (i.e., increasing physical activity, changing dietary consumption, decreasing/eliminating alcohol consumption and smoking, administering therapeutic agents such as lavostatin, pravastatin, simvastatin, fluvastatin, and atorvastatin)) or in the treatment of hypercholesterolemia-related complications, conditions, or diseases.

In other embodiments, a cysteamine compound can be concurrently administered with at least one additional therapeutic agent suitable for use in the treatment of diabetes (i.e., insulin and/or a hypoglycemic compound) or in the treatment of diabetes-associated complications, conditions, or diseases.

In accordance with the subject invention, a therapeutic agent can be provided in admixture with a cysteamine compound, such as in a pharmaceutical composition; or the agent and cysteamine can be provided as separate compounds, such as, for example, separate pharmaceutical compositions administered consecutively, simultaneously, or at different times. Preferably, if the cysteamine compound and the known agent (or therapeutic method) for treating hypercholesterolemia and/or diabetes are administered separately, they are not administered so distant in time from each other that the cysteamine compound and the known agent cannot interact.

As used herein, reference to a "cysteamine compound" includes cysteamine, the various cysteamine salts, which includes pharmaceutically acceptable salts of a cysteamine compound, as well as prodrugs of cysteamine that can, for example, be readily metabolized in the body to produce cysteamine. Also included within the scope of the subject invention are analogs, derivatives, conjugates, and metabolites of cysteamine, which have the ability as, described herein to modulate biological factors in the treatment of a biological condition, prevention of a biological condition in an at-risk patient, or in the treatment of a complication, condition, or disease associated with the biological condition of interest. Various analogs, derivatives, conjugates, and metabolites of cysteamine are well known and readily used by those skilled in the art and include, for example, compounds, compositions and methods of delivery as set forth in U.S. Pat. Nos. 6,521,266; 6,468,522; 5,714,519; and 5,554,655.

Figure 2:
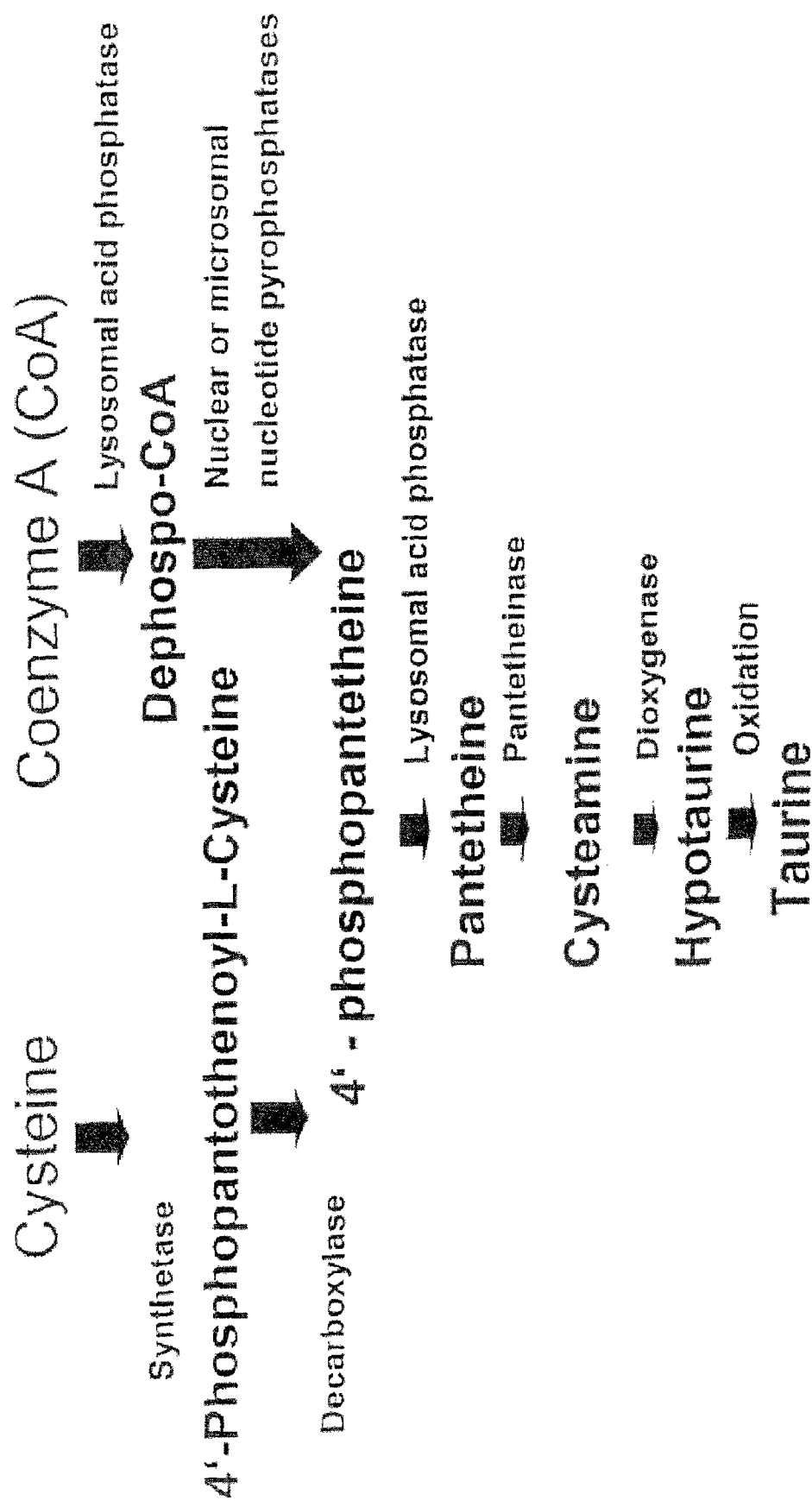
FIG. 2 shows cysteamine as a constituent of co-enzyme A.

As contemplated herein, a cysteamine compound includes compounds that are known to enhance the endogenous production of cysteamine, including pantothenic acid. Pantothenic acid is a naturally occurring vitamin that is converted in mammals to coenzyme A, a substance vital to many physiological reactions. Cysteamine is a component of coenzyme A, and increasing coenzyme A levels results in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine. Accordingly, in one embodiment of the subject invention, the advantages of cysteamine, as set forth herein, can be achieved by promoting the endogenous production of cysteamine through natural metabolic process such as through the action of co-enzyme A or as a metabolite of cysteine (see FIGS. 1 and 2) or administration of pantothenic acid.

The term "pharmaceutically acceptable salt," as used herein, refers to any salt of a cysteamine compound that is pharmaceutically acceptable and does not greatly reduce or inhibit the activity of the cysteamine compound. Suitable examples include acid addition salts, with an organic or inorganic acid such as acetate, tartrate, trifluoroacetate, lactate, maleate, fumarate, citrate, methane, sulfonate, sulfate, phosphate, nitrate, or chloride.

The term "effective amount," as used herein, refers to the amount necessary to elicit the desired biological response. In accordance with the subject invention, the effective amount of a cysteamine compound is the amount necessary to provide an observable effect in at least one biological factor (i.e., observable increase in adiponectin levels) for use in treating a biological condition (such as lowering total blood cholesterol levels in a patient diagnosed with hypercholesterolemia or preventing the onset of diabetes in an at-risk patient). The effective amount may include the amount necessary to enable a 1%-85% decrease in total serum cholesterol levels or blood glucose levels. In certain embodiments, the effective amount enables a 5%, 10%, 20%, 25%, 30%, 35%, 40%, 45%, 50%, 55%, 60%, 65%, 70%, 75%, 80%, 85%, 90%, 95%, 98%, 99% and 100% decrease in severity of complications associated with the biological condition (i.e., diabetes or hypercholesterolemia-related complications such as obesity, retinopathy, glaucoma, cataracts, heart disease, stroke, hypertension, neuropathy, dermopathy, gum disease, etc.).

The present invention provides, for the first time, beneficial materials and methods for modulating a variety of biological factors via the administration of a cysteamine compound. In one embodiment, the materials and methods of the invention treat hypercholesterolemia and/or complications associated with hypercholesterolemia as well as diabetes and/or complications associated with diabetes through the administration of a cysteamine compound to a patient. Specifically exemplified herein is the administration of a cysteamine compound to a patient prior to or after diagnosis of hypercholesterolemia and/or diabetes. In a preferred embodiment, cysteamine hydrochloride (and/or analogs, derivatives and prodrugs thereof) is administered to a patient to treat hypercholesterolemia, diabetes, or complications, conditions, or diseases related to either hypercholesterolemia or diabetes. Preferably, administration of a cysteamine compound (such as cysteamine hydrochloride) is performed at undetermined times.

A cysteamine compound can be administered concurrently with other known agents and/or therapies used to treat diabetes (i.e. insulin, sulfonylureas, biguanides, α-glucosidase inhibitors, thiazolidinediones, meglitinides, D-phenylalanine) and/or hypercholesterolemia- and/or diabetes-associated complications. In other embodiments of the invention, a cysteamine compound can be administered concurrently with materials and/or methods used to treat hypercholesterolemia including, without limitation, amending dietary intake (i.e., reducing the amount of saturated fat and cholesterol in diet); increasing physical activity, decreasing body weight, decreasing or eliminating alcoholic intake/smoking, hormone replacement therapy, and cholesterol lowering medications (i.e., statins, bile acid sequestrants, nicotinic acid, and fabric acids).

In other embodiments, a cysteamine compound can be administered concurrently with materials and/or methods used to treat complications associated with hypercholesterolemia including, without limitation, medications and methods for treating cardiovascular disease (i.e., changes in lifestyle (dietary intake, physical activity, decreasing or eliminating smoking, use of beta-blockers, benazepril, ramipril, and/or torsemide), arteriosclerosis (i.e., changes in lifestyle, use of alpha-adrenergic blockers), atherosclerosis (i.e., changes in lifestyle, use of aspirin or ace inhibitors), stroke (i.e., use of antiplatelet medications, anticoagulant medications), high blood pressure (i.e., changes in lifestyle, use of hypertension medications), pancreatitis (i.e., use of antibiotics, $H_2$-receptor blockers), diabetes (i.e., insulin), and obesity (i.e., changes in dietary intake).

A cysteamine compound can be administered concurrently with insulin to treat type I diabetes, type II diabetes, and related conditions and symptoms. For type II diabetes, insulin resistance, hyperinsulinemia, diabetes-induced hypertension, obesity, or damage to blood vessels, eyes, kidneys, nerves, autonomic nervous system, skin, connective tissue, or immune system, a cysteamine compound may be administered concurrently with a hypoglycemic compound instead of insulin. Alternatively, a cysteamine compound may be administered concurrently with insulin and a hypoglycemic compound to treat type II diabetes, insulin resistance, hyperinsulinemia, diabetes-induced hypertension, obesity, or damage to blood vessels, eyes, kidneys, nerves, autonomic nervous system, skin, connective tissue, or immune system. Additional compounds and/or therapies with which a cysteamine compound can be administered concurrently include, without limitation, gene-based therapies; insulin and methods for administering insulin (i.e., insulin pump, subcutaneous insulin infusion, via inhaler); sulfonylureas (i.e., glyburide, glipizide, glimepiride, tolbutamide, chlorpropramide); insulin secretagogues (i.e., repaglinide, nateglinide); alpha glucosidase inhibitors (i.e., acarbose, miglitol); biguanide; and thiazolidinediones (i.e., rosiglitazone, piaglitazone).

The compositions of the invention can be used in a variety of routes of administration, including, for example, orally-administrable forms such as tablets, capsules or the like, or via parenteral, intravenous, intramuscular, transdermal, buccal, subcutaneous, suppository, or other route. Such compositions are referred to herein generically as "pharmaceutical compositions." Typically, they can be in unit dosage form, namely, in physically discrete units suitable as unitary dosages for human consumption, each unit containing a predetermined quantity of active ingredient calculated to produce the desired therapeutic effect in association with one or more pharmaceutically acceptable other ingredients, i.e., diluent or carrier.

The cysteamine compounds of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, $19^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

In one embodiment, compositions comprising a cysteamine compound and a carrier such as inclusion compound host materials are provided. The "inclusion compound host materials" as described herein, interact with the cysteamine compound to increase aqueous solubility, increase chemical stability, and/or enhance drug (such as cysteamine compound) delivery to and through biological membranes. It is believed that by providing a carrier such as inclusion compound host materials, a stabilized cysteamine compound molecule can be safely delivered to a patient at a dosage that will not induce toxicity. In addition, such carrier materials can include coating materials (i.e., enteric-coatings) that allow dissolution of the coating in an alkaline environment such as in the intestines.

An inclusion compound host material that can be used in accordance with the subject invention include those disclosed in U.S. Patent Application No. 20040033985, incorporated herein in its entirety. Contemplated inclusion compound host materials include proteins (such as albumin), crown ethers, polyoxyalkylenes, polysiloxanes, zeolites, cholestyramine, colestipol, colesevelam, colestimide, sevelamer, cellulose derivatives, dextran derivatives, starch, starch derivatives, and pharmaceutically acceptable salts thereof. Contemplated cellulose derivatives and dextran derivatives include DEAE-cellulose, guanidinoethylcellulose, or DEAE-Sephadex. Favorable starches or starch derivatives to be included in the compositions of the invention include cyclodextrin, retrograded starch, degraded starch, a combination of retrograded and degraded starch, hydrophobic starch, amylase, starch-diethylaminoethylether, and starch-2-hydroxyethylether.

According to the subject invention, preferred inclusion compound host materials include, but are not limited to, cyclodextrin and/or its derivatives (i.e., methyl β-cyclodextrin (M-β-CD), hydropropyl β-cyclodextrin (HP-β-CD), hydroethyl β-cyclodextrin (HE-β-CD), polycyclodextrin, ethyl β-cyclodextrin (E-β-CD) and branched cyclodextrin. As one skilled in the art will appreciate, any cyclodextrin or mixture of cyclodextrins, cyclodextrin polymers, or modified cyclodextrins can be utilized pursuant to the present invention. Cyclodextrins are available from Wacker Biochem Inc., Adrian, Mich. or Cerestar USA, Hammond, Ind., as well as other vendors. Formation of inclusion complexes using cyclodextrin or its derivatives protects the constituent (i.e., cysteamine compound) from loss of evaporation, from attack by oxygen, acids, visible and ultraviolet light and from intra- and intermolecular reactions.

The general chemical formula of cyclodextrin is $(C_6O_5H_9)_n$. The content of inclusion compound host materials in compositions of the subject invention can range from about 1 to 80 wt %. Preferably, the content of inclusion compound host materials in compositions of the invention range from about 1 to 60 wt %. The actual amount of the inclusion compound host materials used will depend largely upon the actual content of cysteamine compound and therapeutic agents, if any, used in preparing compositions of the invention.

Administration of a cysteamine compound, in accordance with the subject invention, can be accomplished by any suitable method and technique presently or prospectively known to those skilled in the art. In a preferred embodiment, a cysteamine compound is formulated in a patentable and easily consumed oral formulation such as a pill, lozenge, tablet, gum, beverage, etc. The consumption is then taken at, prior to, or after, the diagnosis of hypercholesterolemia and/or diabetes.

In accordance with the invention, compositions comprising, as an active ingredient, an effective amount of the cysteamine compound and one or more non-toxic, pharmaceutically acceptable carrier or diluent. Examples of such carriers for use in the invention include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents.

To provide for the administration of such dosages for the desired therapeutic treatment, compositions of the invention for hypercholesterolemia will typically comprise between about 0.1% and 95%, of the total composition including carrier or diluent and for diabetes will typically comprise between about 0.1% and 45%, of the total composition including carrier or diluent. The dosage used can be varied based upon the age, weight, health, or the gender of the individual to be treated.

In certain embodiments of the invention, a patient is assessed to identify the risk of developing insulin dependent diabetes mellitus (IDDM) prior to the concurrent administration of a cysteamine compound and at least one additional therapeutic agent (i.e., physical exercise, improved dietary intake, and reduction in weight). Various markers have recently been identified as important markers that predate the clinical onset of IDDM. Immunological markers that can be detected using methods known to the skilled artisan to assess diabetes susceptibility in asymptomatic patients include, but are not limited to, autoantibodies to insulin (IAA); glutamic acid decarboxylase (GAD); and autoantibodies to islet cells (ICA), such as an islet cell member of the receptor type of the tyrosine phosphate family termed IA-2. Methods for identifying asymptomatic patients susceptible to diabetes by detecting such markers, which can be used in accordance with the subject invention, include, but are not limited to, U.S. Pat. Nos. 6,391,651 and 6,316,209.

In one embodiment, the dosage of a cysteamine compound administered to a patient to modulate a biological factor is about 1 mg/kg of body weight to about 1,000 mg/kg of body weight per day at unscheduled times. Preferably, cysteamine hydrochloride is administered daily at less than about 30 mg/kg of body weight to treat a biological condition.

In one embodiment, cysteamine is administered daily to a patient at unscheduled times to treat diabetes, wherein the therapeutically effective amount of cysteamine is about 0.1 mg to 400 mg per kilogram of patient BW or an equivalent molar quantity of a cysteamine compound. In another embodiment, cysteamine hydrochloride is administered daily to a patient at unscheduled times to treat diabetes, wherein the therapeutically effective amount of cysteamine hydrochloride is about 1.0 mg to 600 mg/kg of BW or an equivalent molar quantity of a cysteamine compound. Preferably, a daily dose of less than about 30 mg/kg of BW of cysteamine, or an equivalent molar quantity of a cysteamine compound, is administered to a patient to treat diabetes in accordance with the present invention.

In an embodiment of the subject invention, the daily dosage amount of a cysteamine compound administered to a patient to treat and/or prevent hypercholesterolemia, or delay the development of hypercholesterolemia-related complications, can be about 1 mg/kg of body weight to 300 mg/kg of body weight. Preferably, a cysteamine compound is administered at about 5 mg/kg of body weight to 150 mg/kg of body weight per day at unscheduled times. In a more preferred embodiment, about 10 mg to 100 mg of cysteamine hydrochloride per kilogram of body weight, or an equivalent molar quantity of a cysteamine compound, is administered daily to a patient.

Following are examples that illustrate procedures for practicing the invention. These examples should not be construed as limiting. All percentages are by weight and all solvent mixture proportions are by volume unless otherwise noted.

Example 1

Nineteen male Goto-Kakizaki Wistar rats (GK rats) with weights of 300±20 g were kept in steel cages, 3-4 rats per cage. The cages were changed every two days. Indoor temperature and relative humidity was kept at 23±3°. and 65±1% respectively. Feed and drinking water was provided. GK rats were permitted a one-month period for adaptation. When the GK rats all demonstrated symptoms of diabetes (i.e., frequent eating, frequent drinking, frequent urination, and high plasma glucose and insulin resistance), they were randomly divided into 3 groups: 7 rats in a control group; 6 rats each in treatment I and II groups.

Prephase Period:

One day prior to experimentation, at 17:00, all of the feed was removed from all groups, but not the drinking water. On the second day, at 09:30, starving plasma glucose was measured for all GK rats. At 10:00, glucose tolerance test (2 g/kg BW) was performed and the plasma glucose level was measured as well for all GK rats. On the third day, the GK rats of the control group were orally administered a saline solution (2 ml/rat) and the GK rats in treatment I and II groups were orally administered a solution of Metformin (17 mg/kg body weight (BW), 2 ml once pre day at 09:30). This regimen was performed for the following several days. On the ninth day, starving plasma glucose was measured and oral glucose tolerance test was performed again for all GK rats in all groups.

Mid-Phase Period:

On the tenth day, the regimen for the GK rats in the treatment II group was changed to an oral administration of Metformin with cysteamine hydrochloride (Metformin 17 mg/kg BW, cysteamine hydrochloride 15 mg/kg BW) for the following 6 days, while the regimen for the control group and the treatment I group remained unchanged. This regimen was performed for six days.

Late-Phase Period:

Six days following the change in regimen, starving plasma glucose was measured and glucose tolerance tests were performed, and blood and tissue samples were collected (liver, duodenum, pancreas gland, fat, and muscle) for all GK rats in all groups. Blood samples were stored at 4° C. for three hours and centrifuged for ten minutes at 3500 rpm. Then, the serum was collected and stored at −20° C. Tissue samples were placed in liquid nitrogen once collected and then stored in −80° C.

The glucose tolerance tests that were performed included the steps of starving the GK rats overnight. Next day at 09:30, starving plasma glucose was measured. At 10:00, oral administration of a glucose solution (2 g/kg BW) was performed. Blood samples were collected via tail vein at 0, 0.5, 1, 2, and 3 hours and then performed with the plasma glucose testing equipment.

The serology testing methods included the steps of measuring serum insulin levels by radioactive measurement; and measuring cholesterol, free fatty acid, and triglyceride using known testing kits and protocol.

Figure 3:
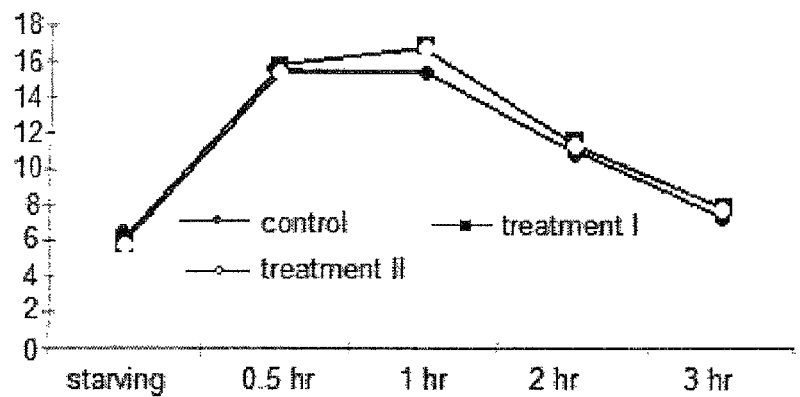
FIGS. 3-5 show results for oral glucose tolerance tests performed on a murine model demonstrating the effectiveness of the materials and methods of the invention.
Figure 4:
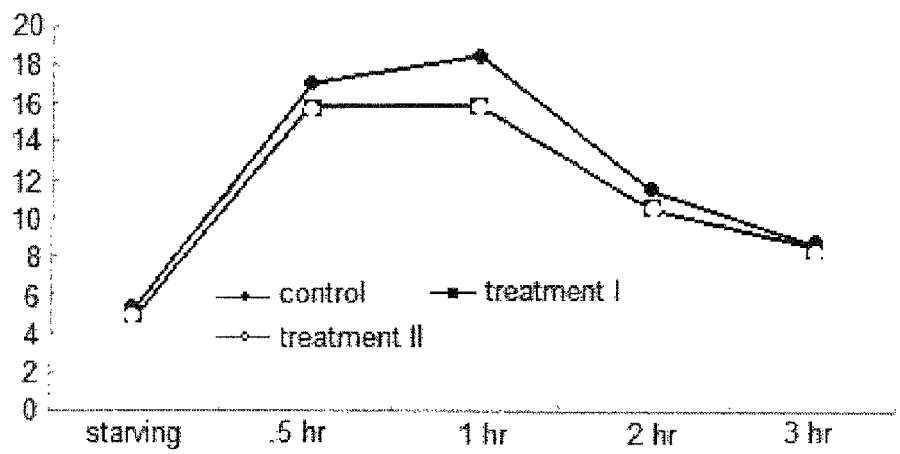
Figure 5:
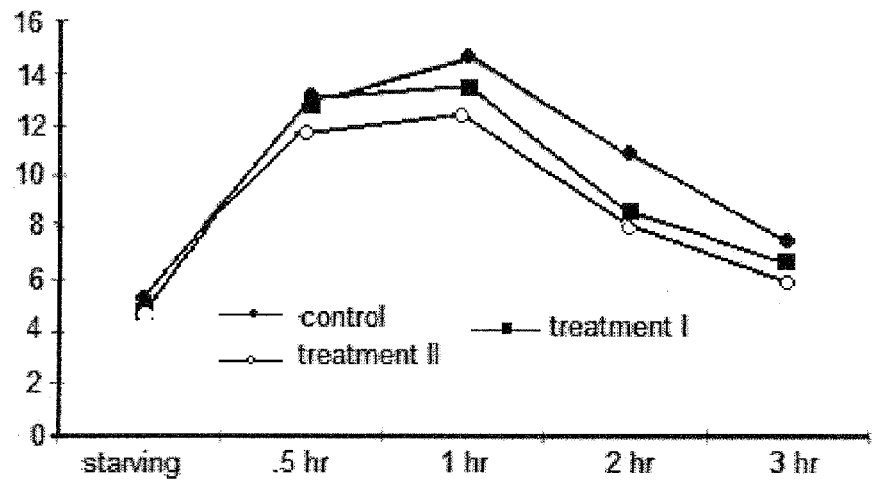
Figure 6:
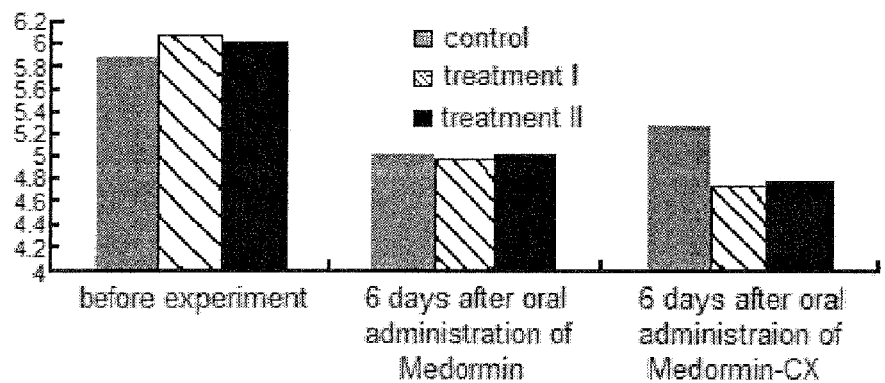
FIG. 6 shows the results of starving plasma glucose tests performed on a murine model demonstrating the effectiveness of the materials and methods of the invention.
Figure 8:
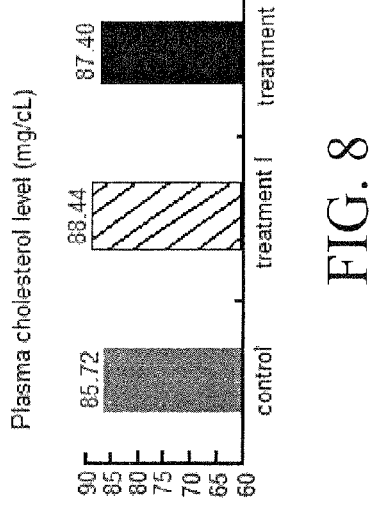
FIG. 7-10 show results from serology tests performed on a murine model demonstrating the effectiveness of the materials and methods of the subject invention.
Figure 10:
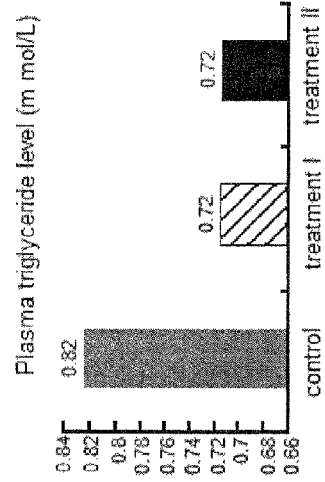
Figure 7:
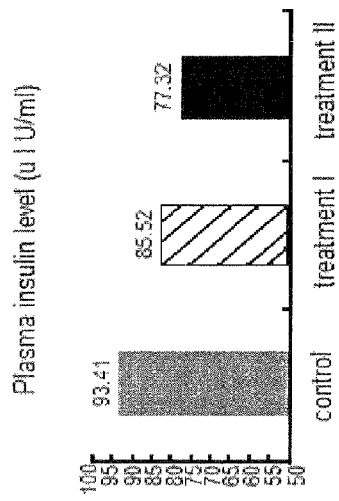
Figure 9:
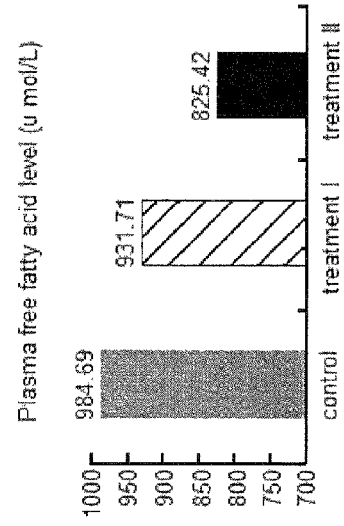

Oral glucose tolerant test results for GK rats in all groups during the pre-phase, mid-phase, and late-phase of the Example are shown in Tables 1, 2 and 3, and FIGS. 3, 4, and 5, respectively. Changes in starving plasma glucose levels during those periods are shown in the tables and summarized in FIG. 6. These results illustrate that the oral administration of Metformin alone, to some extent, lowers duodenal plasma glucose levels and insulin resistance. However, when Metformin is administered concurrently with cysteamine hydrochloride, unexpected, improved results were observed. Specifically, when both Metformin and cysteamine hydrochloride are administered, plasma insulin and free fatty acid levels (indicative of diabetes) were lower than if Metformin (or a cysteamine compound) was administered alone (see FIGS. 7-10). Further, it is expected that lower levels of plasma insulin and free fatty acids would be maintained for a longer period of time after cessation of Metformin/cysteamine hydrochloride administration than if either Metformin or a cysteamine compound were administered alone.

TABLE 1

Glucose tolerance test performed during Pre-Phase

| | Starving | 0.5 hourr | 1 hour | 2 hours | 3 hours |
|---|---|---|---|---|---|
| Control Group | 5.87 | 15.57 | 15.37 | 10.91 | 7.31 |
| Treatment I | 6.08 | 15.74 | 16.76 | 11.4 | 7.82 |
| Treatment II | 6.02 | 15.28 | 16.7 | 11.38 | 7.6 |

TABLE 2

Glucose tolerance test performed during mid-phase (6 days after oral administration of Metformin)

| | Starving | 0.5 hour | 1 hour | 2 hours | 3 hours |
|---|---|---|---|---|---|
| Control Group | 5.03 | 17.04 | 18.46 | 11.5 | 8.59 |
| Treatment I | 4.98 | 15.68 | 15.93 | 10.55 | 8.5 |
| Treatment II | 5.03 | 15.65 | 15.8 | 10.55 | 8.37 |

TABLE 3

Glucose tolerance test performed during late-phase (6 days after oral administration of Metformin + cysteamine hydrochloride)

| | Starving | 0.5 hour | 1 hour | 2 hours | 3 hours |
|---|---|---|---|---|---|
| Control Group | 5.27 | 12.83 | 14.57 | 10.81 | 7.52 |
| Treatment I | 4.75 | 12.98 | 13.42 | 8.6 | 6.67 |
| Treatment II | 4.77 | 11.75 | 12.37 | 8.17 | 6 |

Example 2

Effects of Concurrent Administration of Metformin and a Cysteamine Compound on Non-Diabetic Rats Thirty-two male Wistar rats (purchased from Shanghai Slaccas Laboratory Animal Center) aged about 13 weeks and weighting around 300 g were acclimated to the animal facility for two weeks in individual cages. Food and water were provided ad libitum.

The Wistar rats were divided randomly into 4 groups and each group contained 8 rats. Group 1 (control, n=8) was treated with saline by gavage (2 ml/rat); Group 2 (DC15, n=8) was treated with cysteamine hydrochloride by gavage (15 mg/kg body-weight (BW) in 2 ml tap water); Group 3 (DC22.5, n=8) was treated with cysteamine hydrochloride by gavage (22.5 mg/kg BW in 2 ml tap water); Group 4 (DC30, n=8) was treated with cysteamine hydrochloride by gavage (30 mg/kg BW in 2 ml tap water). All animals were treated at 10:00 for 27 days.

The four groups of animals were kept in the same room in different cages with wire mesh bottoms to reduce coprophagia throughout the experiment. The rats were subjected to fasting overnight on day 28 from 22:00 to 9:30 of the following day. The rats were treated with glucose 2 g/kg BW in 2 ml tap water and the blood was collected from the tail vein at 2 hrs after glucose administration.

Plasma glucose concentrations were determined by Glucotrendr2 equipment (Roche Diagnostics, Basel, Switzerland). Plasma insulin concentrations were determined by radioimmunoassay (Insulin RIA Kit, NO:0410, purchased from Shanghai Radioimmunoassay Research Institution). The effects on fasting plasma glucose and the effects on fasting plasma insulin levels are shown in Table 4. The abbreviation STD denotes the variability of the data about the mean or "standard deviation." The abbreviation p denotes the level of significance of the results.

TABLE 4

Dose-dependent effects of cysteamine hydrochloride on fasting glucose and insulin levels in normal Wistar rats

| Meant ± STD | Control | DC15 | DC22.5 | DC30 |
|---|---|---|---|---|
| Fasting glucose | 4.15 ± 0.18 | 4.05 ± 0.23 | 3.94 ± 0.27 | 3.95 ± 0.17 |
| P | | 0.35 | 0.082 | 0.037 |
| Fasting insulin | 49.62 ± 3.27 | 48.82 ± 3.27 | 48.39 ± 2.38 | 51.32 ± 2.94 |
| P | | 0.55 | 0.27 | 0.2 |

The results obtained for DC30 (Group 4) was statistically different (p=0.037) when compared against the control group (Group 1). Although DC22.5 (Group 3) demonstrated a decrease in blood glucose levels, the results were not statistically significant when compared with the control group (p=0.082).

The results suggest that cysteamine hydrochloride provides a dose-dependent effect on lowering blood glucose levels in normal, fasting Wistar rats. Cysteamine hydrochloride does not affect blood insulin levels in normal, fasting Wistar rats.

Example 3

Effect of Concurrent Administration of Metformin (at a Higher Dose than that of Example 1) and a Cysteamine Compound on Diabetic Rats Thirty-six Goto-Kakizaki Wistar (GK) rats (purchased from Shanghai Slaccas Laboratory Animal Center) aged about 13 weeks and weighting 321-323 g were acclimated to the animal facility for two weeks in individual cages. Food and water were provided ad libitum.

The 36 GK rats were divided into 4 groups based on body weight (BW) and plasma glucose level. Group 1 (control, n=10) was treated with saline by gavage (2 ml/rat); Group 2 (DC, n=6) was treated with cysteamine hydrochloride by gavage (22.5 mg/kg BW in 2 ml tap water); Group 3 (Metformin, Met, n=10) was treated with Metformin by gavage (34 mg/kg BW in 2 ml tap water); Group 4 (Met+DC, n=10) was treated with Metformin 34 mg/kg BW/day in 2 ml tap water for the first 10 days and then was treated with both cysteamine hydrochloride 22.5 mg/kg BW plus Metformin 34 mg/kg BW in 2 ml tap water for the second 10 days. All animals were treated at 10:00 for 20 days.

The four groups of animals were kept in the same room (temp 23±3°., relative humidity 65±1%) in different cages with wire mesh bottoms to reduce coprophagia throughout the experiment. The rats were subjected to fasting overnight from 22:00 to 9:30 of the following day before being subjected to a glucose tolerance test. The rats were treated with glucose 2 g/kg BW in 2 ml tap water at 9:30 for the glucose tolerance test and the blood was collected from the tail vein at 0.5 hr, 1 hr, 2 hr, and 3 hr after glucose injection. Plasma glucose concentrations were determined by Glucotrendr2 equipment (Roche Diagnostics, Basel, Switzerland). Plasma insulin concentrations were determined by radioimmunoassay (Insulin RIA Kit, NO:0410, purchased from Shanghai Radioimmunoassay Research Institution). The effects on plasma glucose levels are shown in Table 5 and the effects on plasma insulin level are shown in Table 6.

With the group that was administered Metformin, the results obtained at 1 hr, 2 hr, and 3 hr are statistically different (p<0.05, denoted as * in the table) from the control group. Where cysteamine hydrochloride was administered concurrently with Metformin, the results obtained at 1 hr, 2 hr, and 3 hr are statistically different (p<0.05, denoted as * in the table) from the group that was administered only Metformin. The results obtained at 0.5 hr for the concurrent administration of Metformin and cysteamine hydrochloride are decreased as compared to the control group (p=0.059, denoted as + in the table).

TABLE 6

Effects of cysteamine hydrochloride (DC) on Insulin (IU/L) and adiponectin (ng/ml) in GK diabetic rats (Mean ± STD,)

|  | Control | DC | Metformin | Metformin + DC |
|---|---|---|---|---|
| Fasting Insulin | 20.69 ± 1.67 | 22.46 ± 2.65 | 18.75 ± 3.98 | 21.08 ± 4.37 |
| P |  | 0.132 | 0.23 | 0.82 |
| Adiponectin | 3922 ± 528 | 4318 ± 590 | 3917 ± 416 | 3743 ± 366 |
| P |  | 0.034 | 0.971 | 0.206 |

The results from Table 6 regarding the glucose levels of the group that was administered Metformin alone at the 1 hr, 2 hr, and 3 hr time points following glucose intake were statistically significantly different from respective control groups. Cysteamine hydrochloride alone did not affect either glucose levels or insulin levels in GK diabetic rats. Administration of Metformin resulted in a decreased, but not statistically significant, insulin level. However, when Metformin was administered concurrently with cysteamine hydrochloride, an improvement in lowering glucose levels (especially when compared against the therapeutic effect of Metformin when administered alone) was observed at all time points except at the Fasting time point.

It was also observed that adiponectin was significantly increased by cysteamine but not Metformin alone. This suggests that the sole administration of a cysteamine compound may be useful in preventing the onset of either diabetes or hypercholesterolemia in at-risk patients since adiponectin plays an important role in the development of either biological condition.

TABLE 7

Effects of cysteamine hydrochloride (DC) and metformin or in combination on glut 4 expression in different tissues of GK diabetic rats (Mean ± STD), expressed as fold changes compared with control level

|  | DC | Metformin | Metformin + DC |
|---|---|---|---|
| liver | 3.77 ± 3.15 | 2.43 ± 1.85 | 2.8 ± 1.0 |
| p | 0.002 | 0.31 | 0.04 |

TABLE 5

Glucose tolerance test for cysteamine hydrochloride (DC) alone and plus Metformin in GK diabetic rats (Mean ± STD, mmol/L)

|  | N | Fasting | 0.5 hr | 1 hr | 2 hr | 3 hr |
|---|---|---|---|---|---|---|
| Control | 10 | 5.56 ± 0.22 | 15.78 ± 1.96 | 15.32 ± 1.58 | 11.52 ± 1.45 | 8.85 ± 0.8 |
| DC | 6 | 5.80 ± 0.36 | 16.68 ± 1.1 | 15.68 ± 0.8 | 11.00 ± 0.8 | 8.33 ± 0.64 |
| Metformin | 10 | 5.53 ± 0.53 | 15.24 ± 1.34 | 13.98 ± 0.95* | 9.62 ± 0.83* | 7.71 ± 1.37* |
| Metformin + DC | 10 | 5.46 ± 0.46 | 14.07 ± 1.84+ | 12.44 ± 0.96* | 7.71 ± 0.83* | 6.35 ± 0.73* |

TABLE 7-continued

Effects of cysteamine hydrochloride (DC) and metformin or in combination on glut 4 expression in different tissues of GK diabetic rats (Mean ± STD), expressed as fold changes compared with control level

|  | DC | Metformin | Metformin + DC |
|---|---|---|---|
| muscle | 1.5 ± 0.74 | 1.38 ± 0.67 | 1.31 ± 0.75 |
| p | 0.001 | 0.152 | 0.633 |
| adipocyte | 2.7 ± 1.16 | 2.14 ± 1.39 | 3.49 ± 2.37 |
| p | 0.005 | 0.095 | 0.095 |

As shown in Tables 5-7, a cysteamine compound (such as cysteamine hydrochloride) can significantly increase the expression of total glut4 in liver, muscles, adipocytes in the GK rats. This increase is much greater in liver and adipocytes as compared to muscles. Such activity suggests that a cysteamine compound may not only be useful in preventing the onset of biological conditions associated with glut4 expression but also in treating biological conditions associated with low glut4 expression. For example, based on these results, a cysteamine compound may be useful in treating complications, conditions, or diseases associated with low glut4 expression.

Metformin alone also increased, but not significantly, the expression levels of total glut4 in all tissues measured. However, the levels of total glucose transporter (glut4) expression were further enhanced when Metformin was concurrently administered with a cysteamine compound.

Example 4

Effect of Administration of a Cysteamine Compound on Diabetic Humans

A small open-label, randomized trial was carried out at the national reference center for diabetes in China. Sixty patients of both sexes (ages ranged from 30 to 75 years old) diagnosed with diabetes type II were recruited. All subjects were informed and gave their consent to participate. Diabetes was diagnosed based on the WHO criteria set in 1999. In addition, patients selected fulfilled the following criteria: (1) a diabetes history of less than 5 years; (2) fasting plasma glucose level between 7-14 mmol/L; (3) serum triglyceride level of 2.5 mmol/L or higher; (4) urine protein excretion of 30 mg/day or higher; and (5) no intake of anti-lipid drugs and ACE inhibitors in the past one month. Patients with the following conditions were excluded from the study: (1) dysfunction of heart, liver and/or kidney; (2) with acute diabetic complications and/or any acute cardiovascular complications or other chronic diseases in the past three months; and (3) pregnancy or nursing.

Patients were divided randomly into four groups of 15 patients each. A control group of subjects was not administered anti-diabetic drugs. The cysteamine alone (DC) group was treated with 540 mg/day of cysteamine hydrochloride. In the Metformin alone (Met) group, the dose of Metformin remained unchanged during the two months period. For the DC+Met group, patients remained on the same dose of Metformin they were originally administered, including an additional 100 mg/day of cysteamine hydrochloride. All patients were subjected to treatments for two months and samples were collected and measured at the beginning of, one month after, and two month after the trial for analysis. The results described herein are derived from the samples collected and measured at the beginning of the first month after the trial.

TABLE 8

Effects of cysteamine hydrochloride on lipid and insulin in diabetic patients

|  | Pre-treatment | n | Post-treatment | n | Paired Difference | 95% CI | p |
|---|---|---|---|---|---|---|---|
| IGF | 49.36 ± 5.75 | 10 | 44.37 ± 7.28 | 10 | 4.99 ± 5.12 | 1.33~8.65 | 0.013 |
| FINS | 35.39 ± 14.43 | 6 | 13.25 ± 6.36 | 6 | 22.14 ± 19.39 | 1.79~42.5 | 0.038 |
| FCP | 739 ± 183 | 7 | 557 ± 119 | 7 | 182 ± 164 | 30.1~333.9 | 0.026 |
| FBS | 7.52 ± 1.57 | 11 | 8.21 ± 2.43 | 11 | −0.69 ± 2.11 | −2.11~0.72 | 0.301 |
| HOMA | 11.94 ± 4.62 | 6 | 5.43 ± 3.19 | 6 | 6.51 ± 4.94 | 1.32~11.7 | 0.023 |
| UA | 389 ± 50.98 | 11 | 359 ± 60.16 | 11 | 29.5 ± 37.87 | 4.07~54.95 | 0.027 |
| 24 h Microalbuminuria | 42.73 ± 31.33 | 8 | 30.97 ± 25.12 | 8 | 11.77 ± 40.73 | −22.28~45.82 | 0.441 |

TABLE 9

Effects of Metformin on lipid and insulin in diabetic patients

|  | Pre-treatment | N | Post-treatment | n | Paired Difference | 95% CI | p |
|---|---|---|---|---|---|---|---|
| IGF | 52.81 ± 10.04 | 10 | 47.32 ± 9.12 | 10 | 5.49 ± 7.23 | 0.32~10.66 | 0.04 |
| FINS | 19.35 ± 10.2 | 5 | 12.33 ± 6.0 | 5 | 7.01 ± 10.23 | −5.69~19.71 | 0.2 |
| FCP | 579 ± 212 | 5 | 693 ± 220 | 5 | −114 ± 295 | −480~253 | 0.437 |
| FBS | 8.92 ± 2.7 | 12 | 8.37 ± 2.03 | 12 | 0.54 ± 2.78 | −1.22~2.3 | 0.512 |
| HOMA | 7.33 ± 3.3 | 5 | 5.35 ± 3.91 | 5 | 1.98 ± 4.47 | −3.57~7.53 | 0.378 |
| UA | 320 ± 67 | 10 | 324 ± 53 | 10 | −4.41 ± 48.7 | −39.22~30.4 | 0.781 |
| 24 h Microalbuminuria | 27.5 ± 23.69 | 8 | 32.86 ± 21.93 | 8 | −5.38 ± 14.36 | −17.39~6.6 | 0.324 |

TABLE 10

Effects of metformin combined with cysteamine on lipid and insulin in diabetic patients

|  | Pre-treatment | n | Post-treatment | n | Paired Difference | 95% CI | p |
|---|---|---|---|---|---|---|---|
| IGF | 55.59 ± 10.48 | 14 | 46.77 ± 4.89 | 14 | 8.83 ± 8.41 | 3.97~13.69 | 0.002 |
| FINS | 22.33 ± 16.59 | 8 | 16.67 ± 9.53 | 8 | 5.66 ± 12.07 | −4.43~15.75 | 0.226 |
| FCP | 752 ± 287 | 8 | 699 ± 388 | 8 | 54 ± 232 | −140~247 | 0.535 |
| FBS | 8.71 ± 1.88 | 13 | 8.9 ± 1.35 | 13 | −0.19 ± 2.14 | −1.48~1.1 | 0.752 |
| HOMA | 9.2 ± 6.99 | 8 | 6.73 ± 4.07 | 8 | 2.46 ± 4.87 | −1.61~6.53 | 0.196 |
| UA | 309 ± 73.7 | 13 | 313 ± 81 | 13 | −4.69 ± 46.93 | −33.05~23.66 | 0.725 |
| 24 h Microalbuminuria | 23.37 ± 21.02 | 9 | 22.11 ± 30.35 | 9 | 1.25 ± 17.98 | −12.56~15.08 | 0.839 |

As shown in Tables 8-10, the administration of cysteamine hydrochloride decreases significantly fasting insulin (FINS), HOMA (Homeostasis Model Assessment), and blood uric acid (UA) levels. In contrast, when Metformin was administered alone, there was only a decrease in IGF-1. Such results suggest that a cysteamine compound can be administered to a patient to improve insulin resistance. Further, the results indicate that administration of cysteamine hydrochloride decreases significantly insulin-like growth factor 1 (IGF1), C peptide (CP), and microalbuminuria (obvious but not statistically significantly) in a patient, which suggests that a cysteamine compound can be used either alone or in combination with additional therapeutic agents to treat or prevent complications associated with diabetes and insulin resistance syndrome. The abbreviation FBS stands for fasting blood sugar.

Example 5

Effect of Cysteamine Hydrochloride in Fat-Feed Rats

TABLE 11

Effects of cysteamine hydrochloride in fat-feed rats (Mean + STD)

|  | Control | DC11.25 | DC22.5 |
|---|---|---|---|
| TG (mmol/L) | 1.22 ± 0.13 | 1.15 ± 0.12 | 1.1 ± 0.08 |
| P |  | 0.236 | 0.024 |
| CH (mmol/L) | 1.88 ± 0.35 | 1.6 ± 0.31 | 1.55 ± 0.27 |
| P |  | 0.071 | 0.029 |
| HDL (mmol/L) | 0.99 ± 0.13 | 1.11 ± 0.16 | 1.04 ± 0.09 |
| P |  | 0.083 | 0.288 |
| LDL (mmol/L) | 0.65 ± 0.17 | 0.61 ± 0.18 | 0.63 ± 0.18 |
| P |  | 0.6 | 0.759 |
| FFA (umol/L) | 1216 ± 236 | 842 ± 256 | 1087 ± 181 |
| P |  | 0.003 | 0.189 |
| UA (mg/L) | 18.49 ± 2.87 | 17.41 ± 1.99 | 16.12 ± 1.04 |
| P |  | 0.342 | 0.024 |

As shown in Table 11, cysteamine at doses of 11.25 mg/kg and 22.5 mg/kg can decrease both triglyceride and cholesterol levels in fat-feed rats. There is a trend that cysteamine can increase HDL and decrease LDL but not significantly in fat-feed rats. Further, cysteamine at doses indicated significantly decrease both uric acid and free fatty acid. These results suggest that administration of a cysteamine compound to a patient at-risk for development of hypercholesterolemia (i.e., a patient with asymptomatic abnormal lipid metabolism) may benefit from such an administration. Moreover, the results suggest that the administration of a cysteamine compound to a patient diagnosed with hypercholesterolemia (or abnormal lipid metabolism) may be have his/her symptoms related to the biological condition alleviated if not eliminated with such a treatment. Moreover, the administration of a cysteamine compound may prove therapeutically effective in delaying or even preventing the onset of any complications, conditions, or diseases associated with abnormal lipid metabolism or hypercholesterolemia.

Example 6

Formulations

The compositions of the invention comprise about 1 to 95 wt % of a cysteamine compound and about 1 to 80 wt % of a carrier such as inclusion compound host materials. In certain embodiments, the compositions of the invention further comprise an additional therapeutic agent of a dosage to ensure therapeutic results when concurrently administered with a cysteamine compound.

In this example, the inclusion compound host materials comprise mainly cyclodextrin and/or its derivative which are selected from a group included methyl β-cycloldextrin (M-β-CD), hydropropyl β-cyclodextrin (HP-β-CD), hydroethyl β-cycloldextrin (HE-β-CD), polycyclodextrin, ethyl β-cyclodextrin (E-β-CD) and branched cycloldextrin. While the workable content of the inclusion compound host materials in the cysteamine-containing composition ranges from 1 to 80 wt %, a preferable workable range of 1 to 60 wt % and a more preferable workable range of 10 to 40 wt % of the inclusion compound host materials may be also be used. The actual amount of the inclusion compound host materials used will depend on the actual content of the cysteamine compound and additional therapeutic agent(s), if any, used in preparing the cysteamine-containing composition.

In certain embodiments, the compositions made according to the present invention are in the form of small granules, each of which has a preferable diameter of substantially 0.28 to 0.90 mm. These granules are prepared using a microencapsulation method. The method involves using a macromolecular substance having inclusion property. One substance that may be used is the inclusion compound host materials (which comprises mainly cyclodextrin) described above. The inclusion compound host materials are a macromolecular substance which acts as a molecular capsule to engulf the molecules of cysteamine and/or additional therapeutic agent(s), whereby the cysteamine compound and/or the therapeutic in the composition are protected and insulated from light, heat, air and moisture of the surroundings. The stability of the cysteamine compound is thus preserved. The inclusion compound host materials used in the micro-encapsulation method are preferably a cyclic polysaccharide compound having 6 to 12 glucose molecules, which is produced by reacting cyclodextrin glycosidtransferase and starch in the presence of Bacillus. Various studies using acute, subacute and chronic toxic tests have shown that the macromolecular substance can reduce toxic levels in a patient. Subsequent to the microencapsulation process, each granule may be coated with at least one and preferably a plurality of layers of the coating materials described above.

The following is an example of how to prepare formulations described above for a cysteamine compound. In a jacketed reactor linked with polytetrafluoroethylene and equipped with a polytetrafluoroethylene coated stirrer, 4080 g of 75 wt % cysteamine hydrochloride solution in ethanol is added with mainly nitrogen being the atmosphere. The purity, melting point and burning residue of the cysteamine used are preferably 98% or above, 66 to 70°. and 0.05% or below respectively. 1200 g β-cyclodextrin is then added into the reactor similarly under the protection of nitrogen gas. (The quality of β-cyclodextrin is in accordance with the requirements for a food additive. In particular, the dry basis purity is more than 98%; the weight loss by drying is less than 10.0%; the burning residue is less than 0.2%; the content of heavy metal is less than 10 ppm; the arsenic content is less than 2 ppm.) The mixture is then heated for 3 hours at 40°. Heating is then stopped and stirring continues for two hours thereafter, products resulted therefrom are then grounded and sieved through a screen (e.g., 40-mesh) filter after the products have been vacuum dried at a temperature of 40-50°. All parts of the equipment, which may come in contact with the ingredients of the composition, should preferably be made of stainless steel.

In a tank-type mixer, 4200 g (on dry basis) of the cysteamine compound, which has undergone the inclusion process as described, 2600 g of the fillers, and 1200 g of the disintegrants and 1700 g binders are added under the protection of a dry surroundings. These ingredients are then thoroughly mixed, and a suitable amount of anhydrous ethanol may be added and then mixed therewith. The resulting mixture presents a soft material with moderate hardness, so that it can be shaped into a ball by a light hold of palms. The ball-shaped resulting mixture may then be broken up by a light touch. After the mixture is pelleted by a granulator under the protection of nitrogen, the small granules resulting therefrom is immediately introduced to a fluid-bed dryer, and is then dried at the temperature of 40-50° C. in a substantially vacuum environment.

Enteric coating materials are then prepared by a method with the following formulation: cellulose acetate phthalate 8.0 g, polyethylene glycol terephthalate 2.4 ml, ethyl acetate 33.0 ml and isopropyl acetate 33.6 ml. The resultant granules obtained above are uniformly coated under the protection of nitrogen with at least one layer but preferably a plurality of layers the enteric coating materials described above. The enteric coating materials are dissolvable only at an alkaline environment. This can prevent the cysteamine compound from prematurely escaped from the composition while it is still in the stomach of the patient. As noted earlier, a cysteamine compound can adversely stimulate gastric mucous of the stomach of a patient.

The resultant granules of the cysteamine-containing composition are then dried completely in a substantially vacuum dryer at a temperature of 40 to 50°. Then, all solvents are removed. The resultant granules are then allowed to cool to room temperature, the micro-capsula were mixed with a suitable amount of flavoring and smelling agents by a cantilever double helix blender. The cystreamine-containing composition is a microcapsule with its interior having cysteamine hydrochloride and cyclodextrin, and with its exterior coated with the enteric coating materials.

The composition produced will exhibit small granular (or micro-particulate) shape having smooth surface, good flow property, and is easy to be blended with various animal feeds. The diameter of each granule of the composition is preferably 0.28 to 0.90 mm. The composition also has excellent stability. It has been found that after the composition is packaged with sealed plastic bags and stored for one year in a cool, dark and dry place, their properties remain unchanged.

The composition having the particular construction described above has a number of functional advantages over a cysteamine compound by itself. Firstly, the activity of the cysteamine compound and additional therapeutic agent(s), if any, contained in the composition is preserved after production. Secondly, the composition should not cause any noticeable gastro side effects to the patient. Thirdly, the activity of the composition is preserved not only during storage but more importantly when traveling through the gastro-tract until it reaches the intestines of the patient.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for increasing adiponectin levels in a patient in need of increased plasma adiponectin levels, said method comprising administering, to a patient who has a decreased plasma adiponectin level, an effective amount of cysteamine, or a salt thereof; wherein the administration of cystaminine, or a salt thereof, results in the increase of plasma adiponectin levels in the patient.

2. The method, according to claim 1, wherein the salt of cysteamine is cysteamine hydrochloride.

3. The method of claim 1, wherein the effective amount of cysteamine, or salt thereof, is about 1.0 mg to about 300 mg per kilogram of body weight daily.

4. The method of claim 3, wherein the effective amount of cysteamine, or salt thereof, is about 5.0 mg to about 150 mg per kilogram of body weight.

5. The method of claim 1, further comprising the step of concurrently administering, with the cysteamine, or salt thereof, another agent selected from the group consisting of lavostatin; pravastatin; simvastatin; fluvastatin; atorvastatin; bile acid resins; nicotine acid; niacin; and fibrates.

6. The method of claim 1, further comprising the step of encapsulating the cysteamine compound in an inclusion compound host material.

7. The method of claim 6, wherein the inclusion compound host material is selected from the group consisting of: proteins; crown ethers; polyoxyalkylenes; polysiloxanes; zeolites; cholestyramine; colestipol; colesevelam; colestimide; sevelamer; cellulose derivatives; dextran derivatives; starch; starch derivatives; and pharmaceutically acceptable salts thereof.

8. The method of claim 7, wherein the inclusion compound host material comprises cyclodextrin.

9. The method of claim 1, wherein the patient is diagnosed with a condition selected from the group consisting of: cardiovascular disease, cerebrovascular thrombosis, cerebrovascular hemorrhage, stroke, coronary thrombosis, intermittent claudication, and ischemia in the limbs.

* * * * *

UNITED STATES PATENT AND TRADEMARK OFFICE
CERTIFICATE OF CORRECTION

PATENT NO. : 8,372,889 B2
APPLICATION NO. : 12/956576
DATED : February 12, 2013
INVENTOR(S) : Bill Piu Chan et al.

Page 1 of 1

It is certified that error appears in the above-identified patent and that said Letters Patent is hereby corrected as shown below:

In the Specifications

Column 18,
Line 49, "23±3°" should read --23±3°C--

Column 21,
Line 39, "23±3°" should read --23±3°C--

Column 27,
Line 13, "60 to 70°, and" should read --60 to 70°C and--

Column 27,
Line 20, "3 hours at 40°" should read --3 hours at 40°C--

Column 27,
Line 24, "40 to 50°" should read --40 to 50°C--

Column 27,
Lines 57, "40 to 50°" should read --40 to 50°C--

Signed and Sealed this
Twenty-eighth Day of May, 2013

Teresa Stanek Rea
*Acting Director of the United States Patent and Trademark Office*